United States Patent
Sharma et al.

(10) Patent No.: US 8,686,869 B2
(45) Date of Patent: Apr. 1, 2014

(54) ALIGNMENT-RELATED OPERATION AND POSITION SENSING OF ELECTRONIC AND OTHER LOCKS AND OTHER OBJECTS

(75) Inventors: Arun Kumar Sharma, Cupertino, CA (US); David Arthur Candee, Milpitas, CA (US)

(73) Assignee: SecureALL Corporation, Mountain View, CA (US)

( * ) Notice: Subject to any disclaimer, the term of this patent is extended or adjusted under 35 U.S.C. 154(b) by 11 days.

(21) Appl. No.: 13/340,031

(22) Filed: Dec. 29, 2011

(65) Prior Publication Data

US 2012/0167646 A1   Jul. 5, 2012

Related U.S. Application Data

(60) Provisional application No. 61/428,093, filed on Dec. 29, 2010.

(51) Int. Cl.
  *G08B 21/00*  (2006.01)
(52) U.S. Cl.
  USPC .......... 340/686.2; 292/251.5; 70/276; 70/413
(58) Field of Classification Search
  USPC ............... 340/686.2; 292/251.5; 70/262, 264, 70/266, 275, 276, 277, 278.1, 279.1–283, 70/333, 431, 432, 461, 466
  See application file for complete search history.

(56) References Cited

U.S. PATENT DOCUMENTS

| | | | |
|---|---|---|---|
| 4,744,021 A | 5/1988 | Kristy | |
| 4,774,494 A | 9/1988 | Extance et al. | |
| 5,422,479 A | 6/1995 | Sahori | |
| 6,441,735 B1 | 8/2002 | Marko et al. | |
| 6,474,120 B1 * | 11/2002 | Wadsworth et al. | 70/276 |
| 7,908,896 B1 * | 3/2011 | Olson et al. | 70/278.1 |
| 2006/0164208 A1 | 7/2006 | Schaffzin et al. | |
| 2007/0209413 A1 | 9/2007 | Dobbs | |
| 2008/0012359 A1 | 1/2008 | Aschieri | |

(Continued)

FOREIGN PATENT DOCUMENTS

WO   WO 2006/078362 A2   7/2006

OTHER PUBLICATIONS

PCT International Search Report mailed Aug. 30, 2012 for International Patent Application No. PCT/US2011/067890 filed Dec. 29, 2011, 4 pages total.

(Continued)

*Primary Examiner* — Brian Zimmerman
*Assistant Examiner* — Laura Nguyen
(74) *Attorney, Agent, or Firm* — Haynes and Boone LLP

(57) ABSTRACT

A sensing system senses whether or not a lock's bolt (140), e.g. deadbolt, is aligned with a hole (150) which the bolt is to engage in the locked state. In electronic locks, the bolt is not driven into the hole until the sensing system indicates that the bolt is aligned with the hole. Another sensing system senses the position of the bolt and/or a dead-latch bar (1310). This sensing system is spaced from the bolt's end engaging the hole in order not to interfere with the alignment sensing. The two sensing systems are used to determine whether the lock is locked or unlocked. A magnet system provides alignment assistance to align the bolt with the hole before the bolt is driven into the hole. Position encoding for lock and non-lock devices, and other features and embodiments are also provided.

28 Claims, 28 Drawing Sheets

(56) References Cited

U.S. PATENT DOCUMENTS

| | | |
|---|---|---|
| 2008/0209228 A1 | 8/2008 | Chandler |
| 2009/0090148 A1 | 4/2009 | Kollin et al. |
| 2012/0119523 A1* | 5/2012 | Burdenko et al. ......... 292/251.5 |

OTHER PUBLICATIONS

PCT Written Opinion mailed Aug. 30, 2012 for International Patent Application No. PCT/US2011/067890 filed Dec. 29, 2011, 6 pages total.

Stanley Security Solutions, Integrated Solutions Guest Housing, Best Access Systems, 2006, 8 pages.

RCI Installation Instructions, Rutherford Controls Int'l Corp., Fail Locked 3108, Fail Unlocked 3308, Electric Deadbolt, 2011, 2 pages.

3108-3308—Rutherford Controls, product information, retrieved Oct. 3, 2011, 3 pages. http://www.rutherfordcontrols.com/products/electric-locks/3108-3308.

3108-3308—Rutherford Controls, standard features, retrieved Oct. 3, 2011, 2 pages. http://www.rutherfordcontrols.com/products/electric-locks/3108-3308.

* cited by examiner

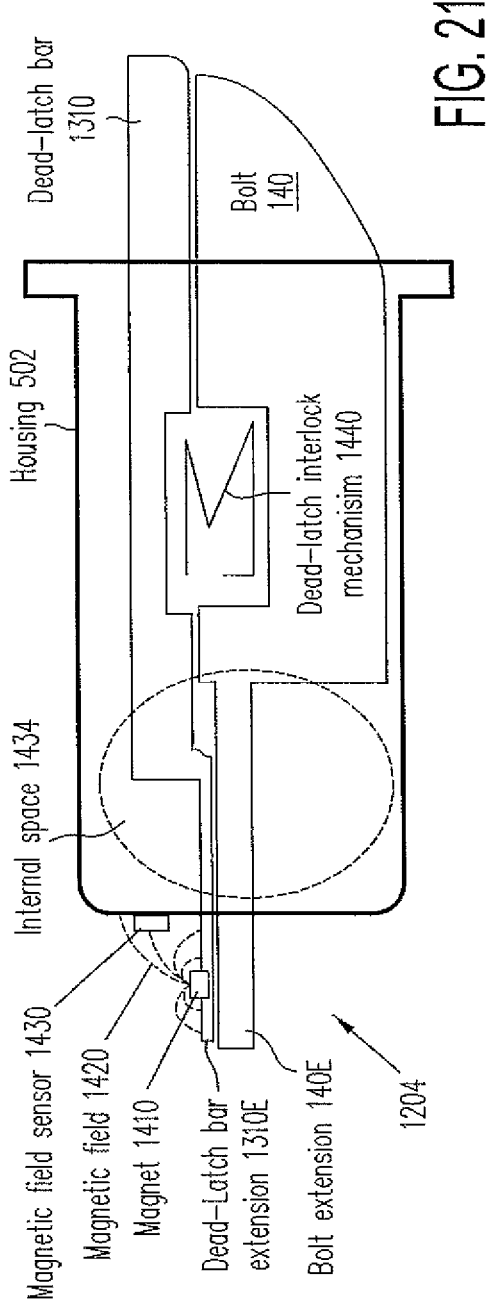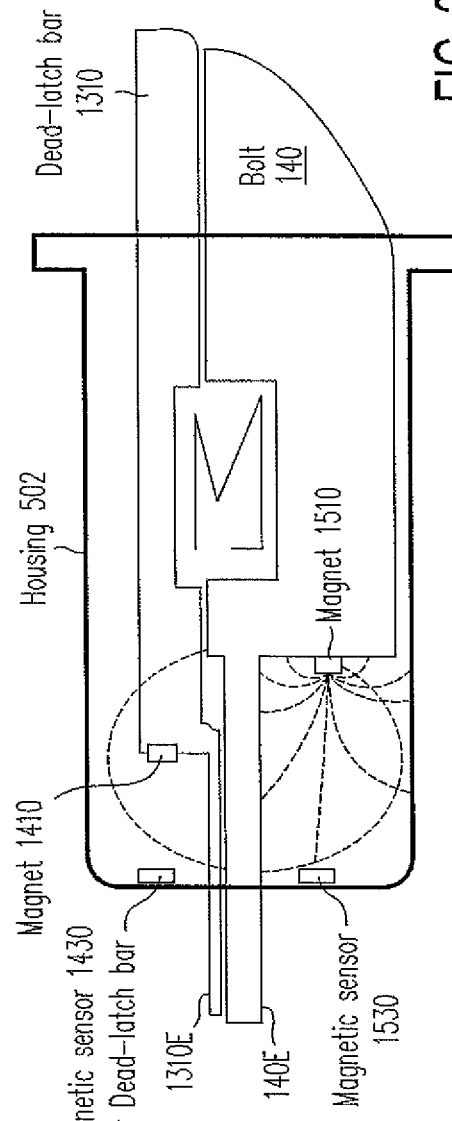

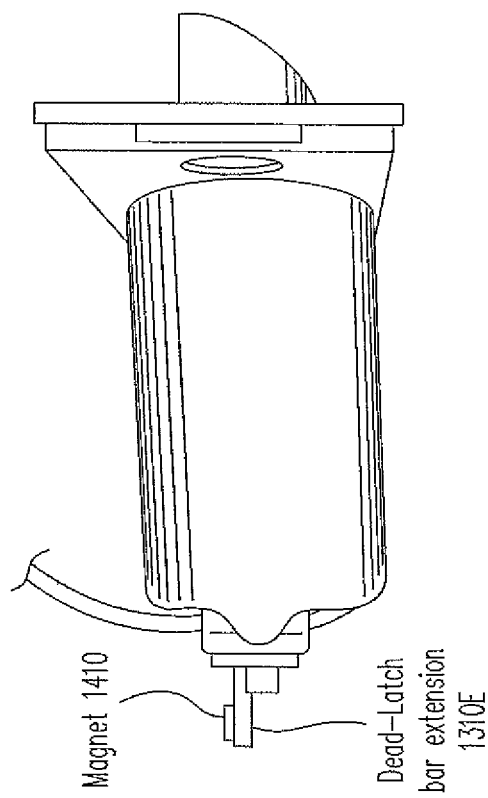
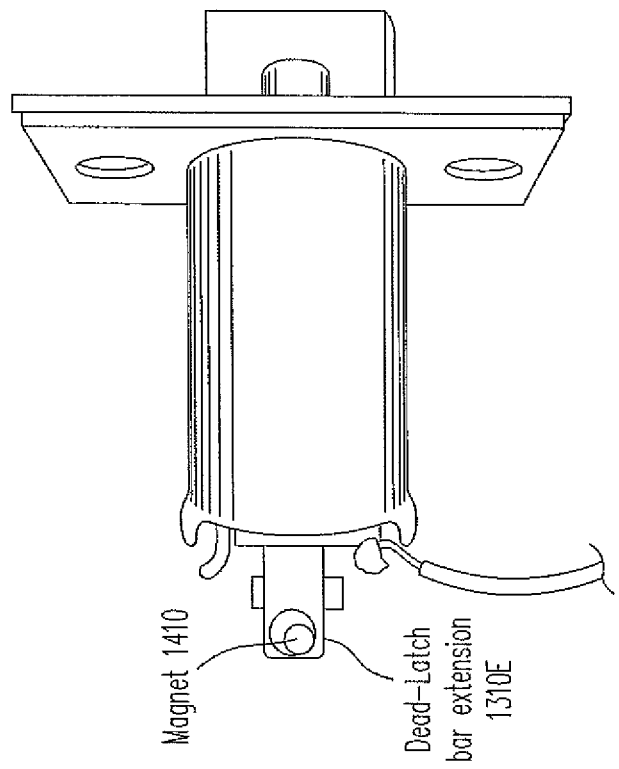

ALIGNMENT-RELATED OPERATION AND POSITION SENSING OF ELECTRONIC AND OTHER LOCKS AND OTHER OBJECTS

CROSS-REFERENCE TO RELATED APPLICATIONS

The present invention claims priority of U.S. provisional patent application No. 61/428,093, filed Dec. 29, 2010, incorporated herein by reference.

BACKGROUND OF THE INVENTION

The present invention relates to alignment and position sensing of locks and other objects. While the invention is applicable to different types of objects, some aspects of the invention were motivated by electronic deadbolt locks.

Unlike spring bolts which are spring-biased into an extended (locked) position, a deadbolt is not biased, and has to be extended by turning a key or a knob or, in electronic operation, by an electro-mechanical actuator (e.g. motor, solenoid, etc.). When a door with a spring-bolt lock is being closed, the door jamb pushes the spring bolt into the door and the spring bolt retracts. In contrast, the deadbolt does not need to retract when pushed against the door jamb, and therefore deadbolts can be heavier and stronger to provide greater security against lock picking.

U.S. Pat. No. 4,744,021 issued May 10, 1988 to Kristy describes a computer-controlled electronic deadbolt for a vehicle door. A computer-controlled motor extends or retracts the deadbolt in response to a push-button-activated signal from a transmitter. When the deadbolt meets an obstruction while being extended or retracted, the motor slows or stops, and the motor's current flow increases. This condition is sensed to energize an obstruction indicator such as a buzzer.

SUMMARY

This section summarizes some features of the invention. Other features may be described in the subsequent sections. The invention is defined by the appended claims, which are incorporated into this section by reference.

An obstruction indicator such as a buzzer is ineffective in many situations, for example when the lock is installed in a public building where people may not understand the buzzer significance or may be unwilling to take time and remove the obstruction. In any case, whether or not a buzzer is appropriate, some embodiments of the invention provide an alignment system for sensing the alignment between the deadbolt and a hole (a cavity) into which the deadbolt is to extend. The lock's actuator does not attempt to extend the deadbolt until the alignment system indicates alignment between the deadbolt and the cavity. Therefore, the actuator is not stressed by being driven against an obstruction, so mechanical wear and tear are reduced, and electric power is not wasted.

Conserving electrical power is particularly desirable for battery-powered electronic locks such as described, for example, in U.S. patent application Ser. No. 11/035,636 filed Jan. 14, 2005 by Schaffzin et al. and published as US2006/0164208 on Jul. 27, 2006, incorporated herein by reference.

According to some embodiments of the invention, the alignment system provides more than just coarse sensing of whether or not the door is closed because even a closed door may be slightly misaligned to cause the deadbolt to be obstructed. In some embodiments, an optical sensor is used. The alignment system may emit light from the deadbolt itself, and the light is matched with a light sensor installed in the cavity. Alternatively, the light emitting port may be in the cavity and the sensor in the deadbolt. In still another alternative, both the light emitting port and the light receiver (for the sensor) may be provided on the deadbolt side of the lock and may be matched with a reflector in the cavity, or the light emitting port and the light receiving port may be in the cavity and the reflector may be in the deadbolt. Magnetic sensors and other types of sensors can also be used.

The invention is not limited to deadbolts but is applicable to spring bolts and other types of fasteners. Further, the invention includes light-sensor aspects applicable to position encoding for robots and other kinds of devices.

In addition, some embodiments provide an alignment assisting device ("alignment assist"), e.g. a matching set of magnets installed immediately adjacent to the fastener and the cavity, to urge a closed or partially-closed door into an aligned state.

It is known to provide a spring-bolt lock with a spring-loaded dead-lock bar which can be retracted or extended together with the spring bolt. When the door is being closed, both the spring bolt and the dead-lock bar are first pushed into the retracted position by the door jamb (or a strike plate installed on the door jamb). Then the spring bolt meets the cavity and extends, but the dead-lock bar remains retracted. In this condition—with the spring bolt extended and the dead-lock bar retracted—the spring bolt cannot be pushed from the outside into the retracted position. Therefore, the lock cannot be picked by pressing on the spring bolt with a plastic card, a pin, or a thin metal strip. This type of lock is called a "dead latch" herein.

In some dead latches according to the present invention, the state of the lock is sensed by sensing the positions of the spring bolt and/or the dead-latch bar. Sensing the bolt state is widely used for detecting unauthorized entry. Some prior techniques for sensing the bolt state are described in U.S. patent application Ser. No. 11/867,017 filed 4 Oct. 2007 by Kollin et al., published as no. 2009/0090148 on Apr. 9, 2009. See also U.S. Pat. No. 6,441,735 issued Aug. 27, 2002 to Marko et al. These prior techniques sense the state of a magnetic circuit passing through the lock (possibly through bolt mounting screws and the bolt) and also passing through the door jamb.

In some embodiments of the present invention, the state of the bolt and/or the dead-latch bar is sensed by magnets and sensors installed away from the door jamb, e.g. on the opposite side of the lock. This can provide a self-contained sensing mechanism which does not require a strike plate modification as in some prior art mechanisms. This sensing does not interfere with the alignment sensing described above, and can be combined with the alignment sensing if desired.

The invention is not limited to the features and advantages described above except as defined by the appended claims.

BRIEF DESCRIPTION OF THE DRAWINGS

FIG. 18 is a schematic illustration of a magnetic sensing system that senses alignment between a bolt and a door cavity according to some embodiments of the present invention.

FIGS. 21 and 22 are each a schematic side view of a system which senses the dead latch's state according to some embodiments of the present invention.

FIGS. 26, 27, 28A, 28B, 28C, 28D illustrate back ends of dead latches according to some embodiments of the present invention.

DESCRIPTION OF SOME EMBODIMENTS

The embodiments described in this section illustrate but do not limit the invention. In particular, the invention is not limited to particular dimensions or other details except as defined by the appended claims.

Figure 1:
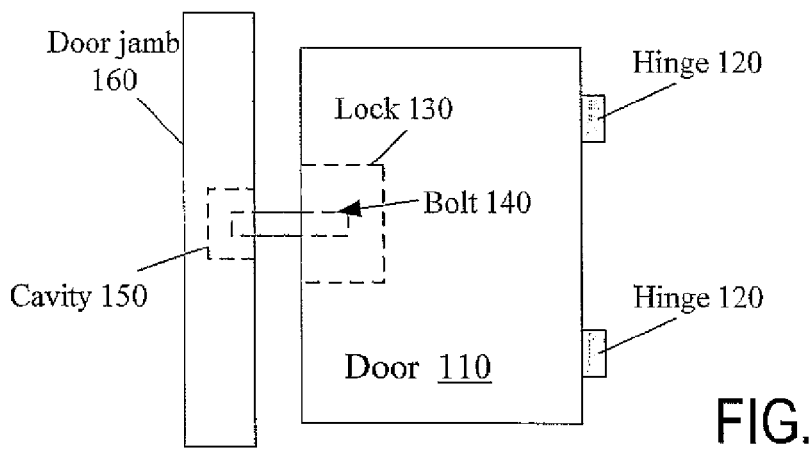
FIG. 1 is a schematic side view of a door locking system used in prior art and in some embodiments of the present invention.

Some embodiments will now be described for a conventional door lock arrangement shown in FIG. 1. A vertical door 110 swings on hinges 120 between an open position and a closed position. When the door is closed, its left edge faces a stationary door jamb 160. A lock 130 includes a bolt (plunger) 140 which extends from the lock's housing into a cavity 150 in door jamb 160 to lock the door. To unlock the door, the bolt 140 is retracted from cavity 150.

Figure 2:
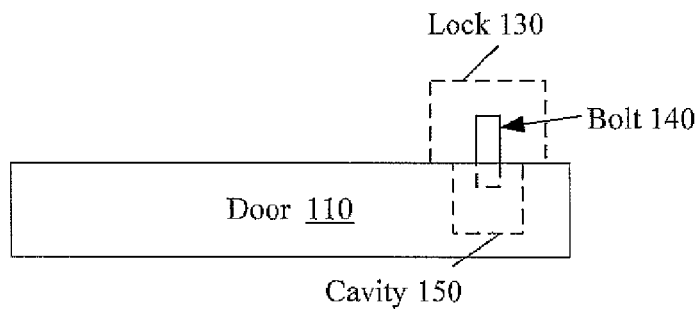
FIG. 2 is a top view of a door locking system used in prior art and in some embodiments of the present invention.

The invention is not limited to this arrangement however. Lock 130 may be installed in the door jamb, with cavity 150 located in door 110. Lock 130 may be installed at the top or bottom of door 110, and bolt 140 can move vertically to engage a cavity in the door if the bolt is mounted on the door frame or on the floor or the ceiling. The bolt 140 can also be installed in the door and can move vertically to engage a cavity in the top or bottom portion of the door frame or in the floor or ceiling. The lock may be installed in a sliding door as in the top view of FIG. 2. Here door 110 slides to the right and left. Bolt 140 is horizontal, and moves into and out of the door's cavity 150. Lock 130 may be positioned on the floor or ceiling near the door, or on a wall portion adjacent to the door, or in some other way. In some embodiments, lock 130 locks double doors together. The lock can be installed in a building, a vehicle, a fence, a safe, a shed, a manhole, a door of a vending machine, a laptop computer (to lock the computer screen to the keyboard), or in other places as needed. Bolt 140 can be replaced by other types of fasteners, e.g. circular fasteners rotating around an axis to engage a cavity.

Figure 3:
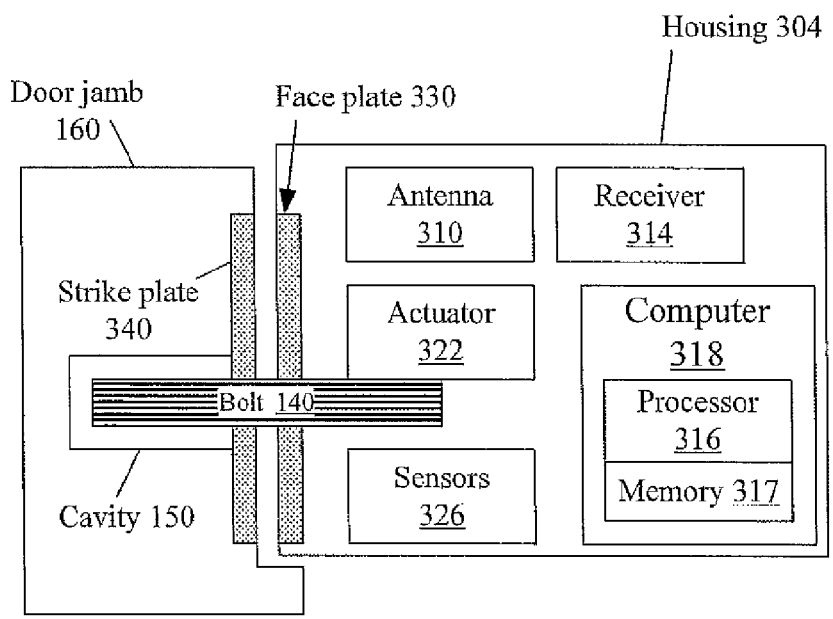
FIG. 3 is a schematic side view and a block diagram of a door locking system according to some embodiments of the present invention.
Figure 4:
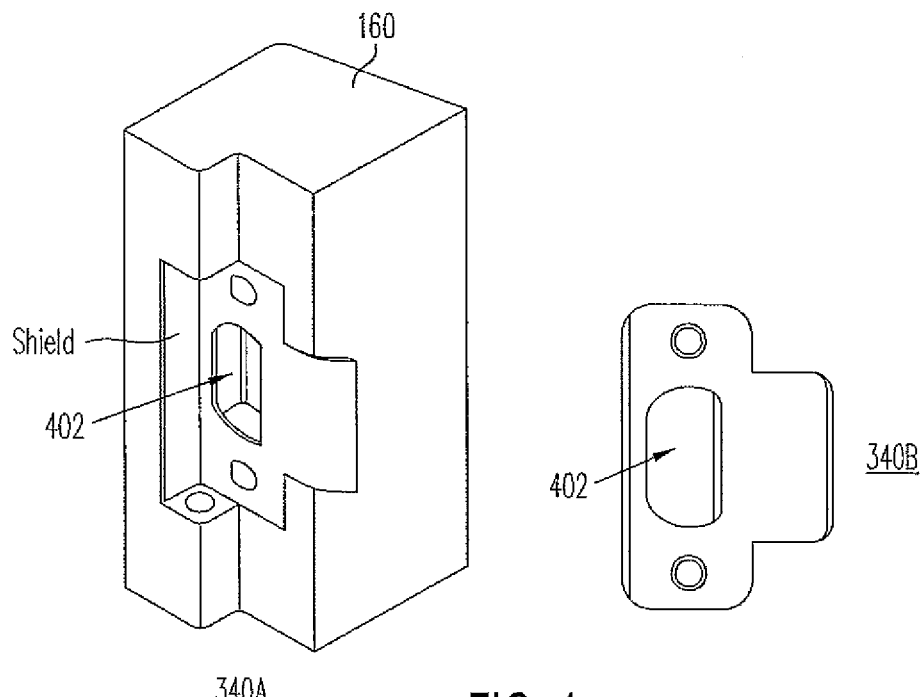
FIG. 4 is a perspective view and a front view of a strike plate used in prior art and in some embodiments of the present invention.

FIG. 3 is a schematic illustration of one embodiment which is an improvement on a lock disclosed in the aforementioned U.S. patent application Ser. No. 11/035,636. Electronic lock 130 of FIG. 3 includes a housing 304 into which the bolt 140 can retract. Within housing 304 are an antenna 310 and a receiver 314 which together detect a signal from an electronic key (e.g. a smart card, not shown). A computer processor 316 in computer 318 (e.g. a microcomputer, possibly also containing memory 317) recognizes the signal and causes an actuator 322 (e.g. an electromechanical device such as a motor, or solenoid, etc.) to extend the bolt 140 if the sensor or sensors 326 show that the bolt is aligned with cavity 150. The bolt extends out through a passage (a hole) in face plate 330 attached to housing 304. Door jamb 160 can be provided with a strike plate 340 with a hole aligned with cavity 150 in the door jamb. Two exemplary (non-limiting) strike plates are shown in FIG. 4 at 340A and 340B. Strike plate 340A has an extension which serves as a shield positioned on the door jamb's protrusion. This protrusion serves as a door stop which allows the door to open in only one direction. Each strike plate has a hole 402 through which the bolt 140 enters the cavity 150 in the door jamb. This construction is exemplary and is not limiting for the present invention.

Bolt 140 is alternatively called a "plunger".

Figure 5:
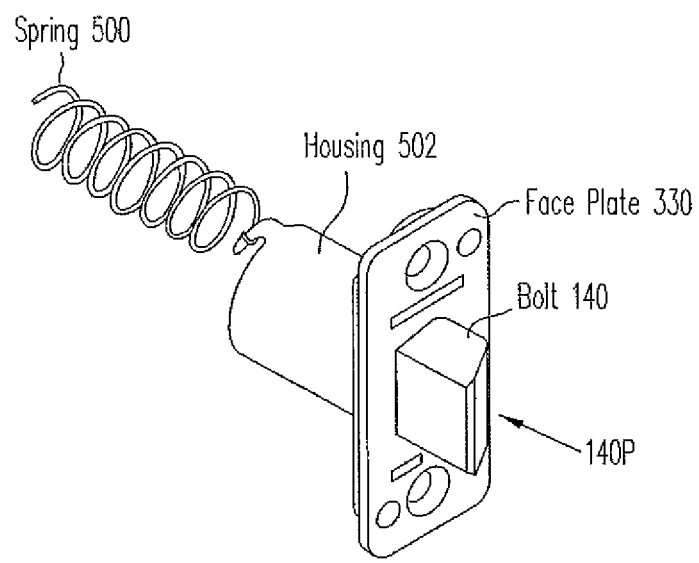
FIG. 5 is a perspective view of a spring-bolt lock used in prior art and in some embodiments of the present invention.

FIG. 5 is a perspective view of a lock 130 of a spring latch type. The spring is shown schematically at 500 and can be located outside a housing 502 but inside housing 304 of FIG. 3. Housing 502 can be inside or outside of housing 304. Bolt 140 has a slanted profile 140P on the side on which the bolt meets the strike plate when the door is being closed. The slanted profile allows the bolt to be pushed into the retracted position by the strike plate.

Figure 6:
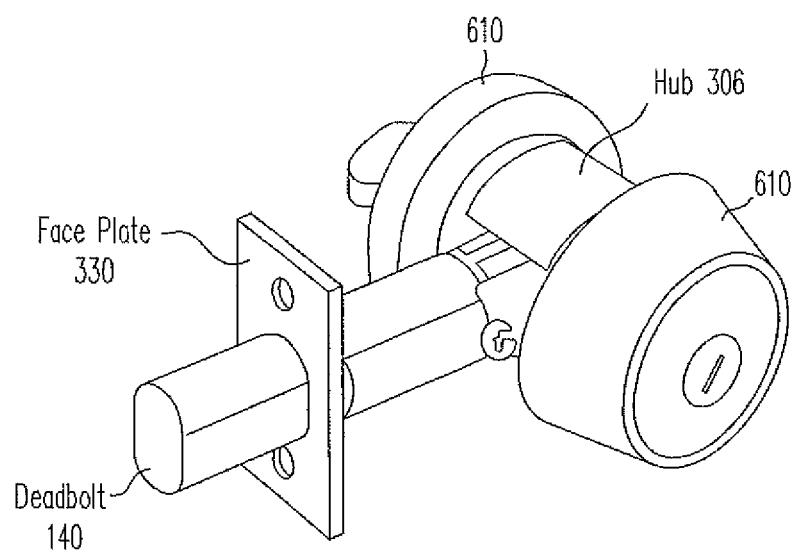
FIG. 6 is a perspective view of a deadbolt lock used in prior art and in some embodiments of the present invention.

FIG. 6 is a perspective view of a deadbolt lock 130, with handles 610 on both sides of the door (the door is not shown). A typical deadbolt does not have a slanted profile but has a flat face on the side facing the strike plate as well as the opposite side.

Alignment Sensing

Figure 7:
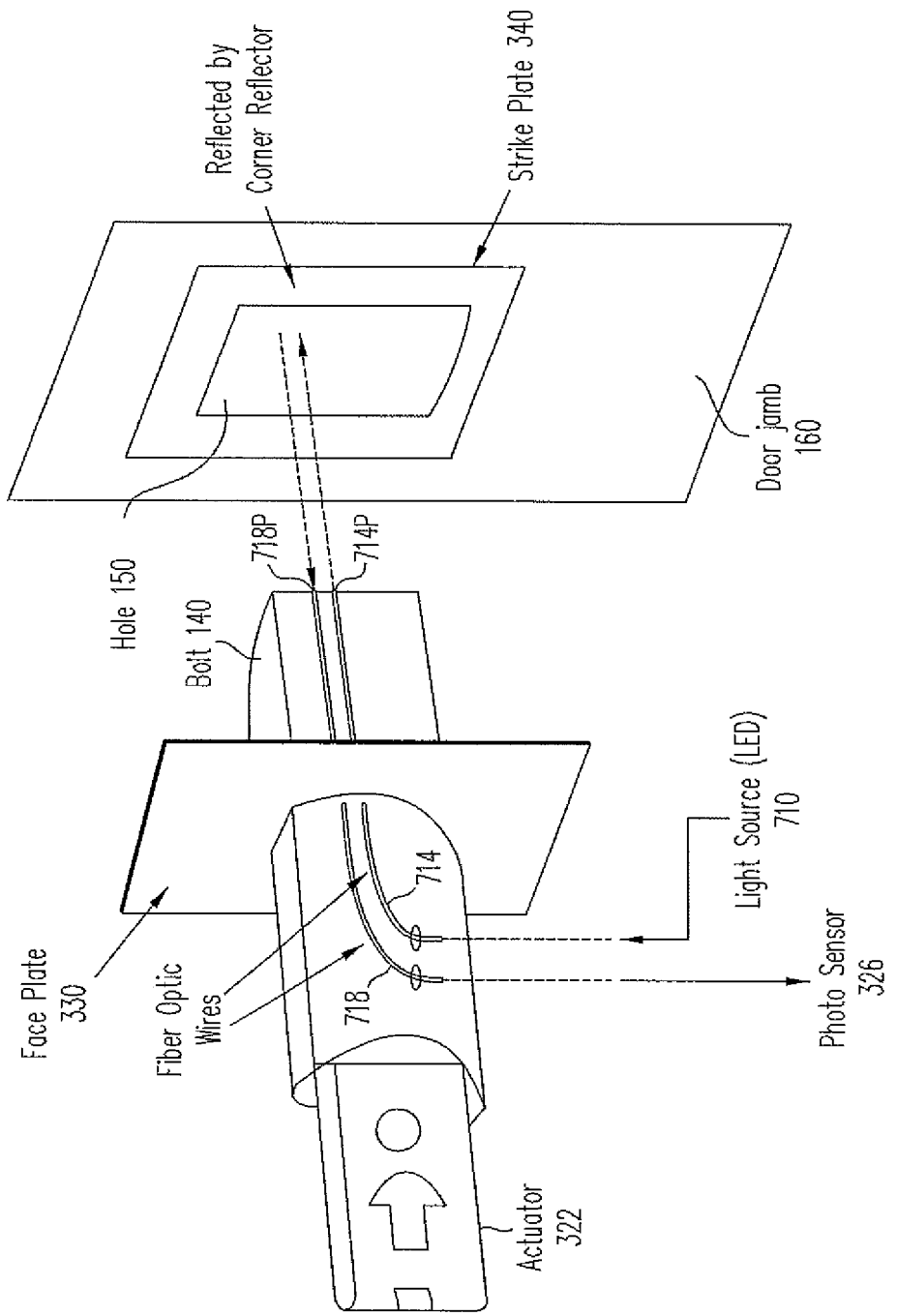
FIG. 7 is a schematic perspective illustration of an optical sensing system that senses alignment between a bolt and a door cavity according to some embodiments of the present invention.

FIG. 7 illustrates alignment sensing between bolt 140 and cavity 150 according to some embodiments of the present invention. The alignment is sensed by means of optical reflection. The terms "optical" and "photo" as used herein are not limited to visible light, but may denote visible or invisible electromagnetic radiation. A light source 710, e.g. a light emitting diode (possibly a laser) or some other type, provides a light beam that is guided by a waveguide 714. We will use the term "light source" to refer either to source 710 or to output port 714P of waveguide 714. In the aligned state, the light emitted at port 714P is reflected by a reflector, not shown in FIG. 7 but shown at 810 in FIG. 8A. The reflector could be a corner reflector as in FIG. 8A, or a flat mirror, or a diffused reflector (e.g. a piece of paper or a label with a reflective portion surrounding by light absorbing material for higher contrast—such reflectors can be less expensive and easier to install than a corner reflector). The reflected light is picked up by input port 718P of waveguide 718. Waveguide 718 guides the reflected light to light sensor 326. Light source 710 is controlled by computer 318, and the computer receives the signals from sensors 326. In some embodiments, for robust operation in the presence of ambient light, the light source 710 modulates the light such that the light sensor signal generated by sensor 326 for computer 318 is correlated to the transmitted light. Thus, in some embodiments, light source 710 is intermittently turned on and off; the sensor senses the ambient light when the light source is off, and computer 318 compares the sensor's ambient-light signal with the sensor's signal obtained when the light source is on. The differential signal is used to determine whether the light source is aligned with the reflector. In some embodiments, the differential signal is generated by a separate integrated circuit comprising the sensor.

Waveguides 714, 718 are, for example, fiber optic wires located on the surface of bolt 140, e.g. in grooves in the bolt's surface. The invention is not limited to fiber optics. In some embodiments, waveguide 714 is omitted, and the light source 710 is positioned at the location of output port 714P, and is connected to computer 318 by electrical wires. Likewise, sensor 326 can be positioned at the location of input port 718P of waveguide 718, and can be connected to computer 318 by suitable wiring. Waveguide 718 can be omitted. In another embodiment (FIG. 8A), waveguides 714 and 718 run through passages inside bolt 140.

In all such embodiments, when bolt 140 is aligned with cavity 150, the light from source 710 is reflected by reflector 810 (not shown in FIG. 7) located in cavity 150. The reflected light is picked up by waveguide 718 or directly by light sensor 326 (if the sensor is installed on the bolt's surface facing the cavity or on face plate 330). The sensor generates a signal recognized by computer 318. In response to this signal, computer 318 causes the bolt to extend if the door needs to be locked.

Figure 8A:
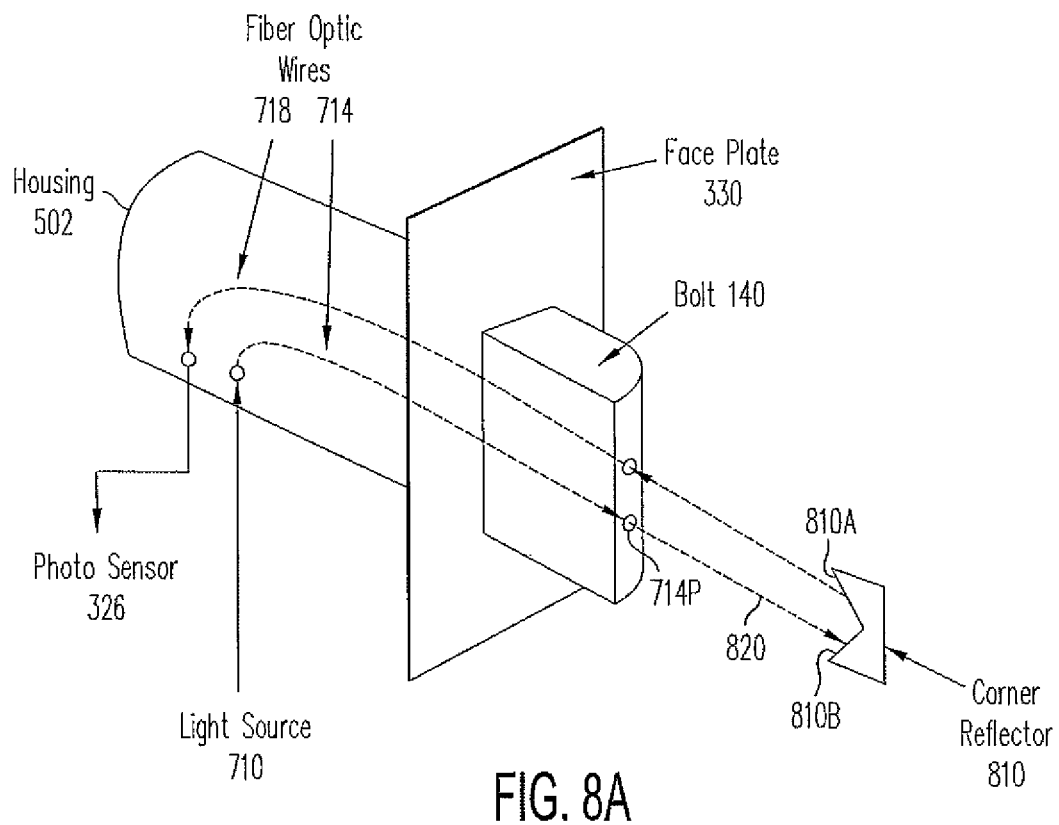
FIG. 8A is a schematic perspective illustration of another optical sensing system that senses alignment between a bolt and a door cavity according to some embodiments of the present invention.

In the embodiment of FIG. 8A, the reflector 810 is a 2D or 3D corner reflector whose light-receiving and light-emitting surfaces 810A, 810B are perpendicular to each other and face the light beam 820 emitted from port 714P. The corner reflector is installed in cavity 150. Other types of reflectors are also possible, including various retro-reflectors, prisms, elliptic and other shapes, and the reflector may include multiple pieces which guide the reflected light to waveguide 718 in the aligned state (i.e. when the bolt is aligned with the cavity).

Figure 8B:
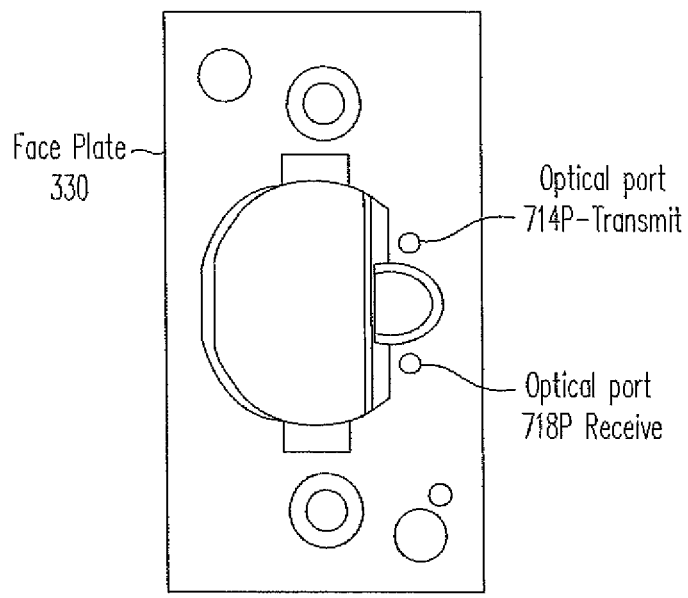
FIG. 8B is a side view of a lock with an optical sensing system for alignment sensing according to some embodiments of the present invention.

FIG. 8B shows a similar embodiment in which the light emitting port 714P and the light receiving port 718P are positioned on face plate 330 close to bolt 140. The reflector (not shown) is in cavity 150 or on strike plate 340 or some other position on door jamb 160. The light emitting port 714P and the light receiving port 718P could optionally be located very close to each other (e.g. at 1 mm distance).

Figure 9:
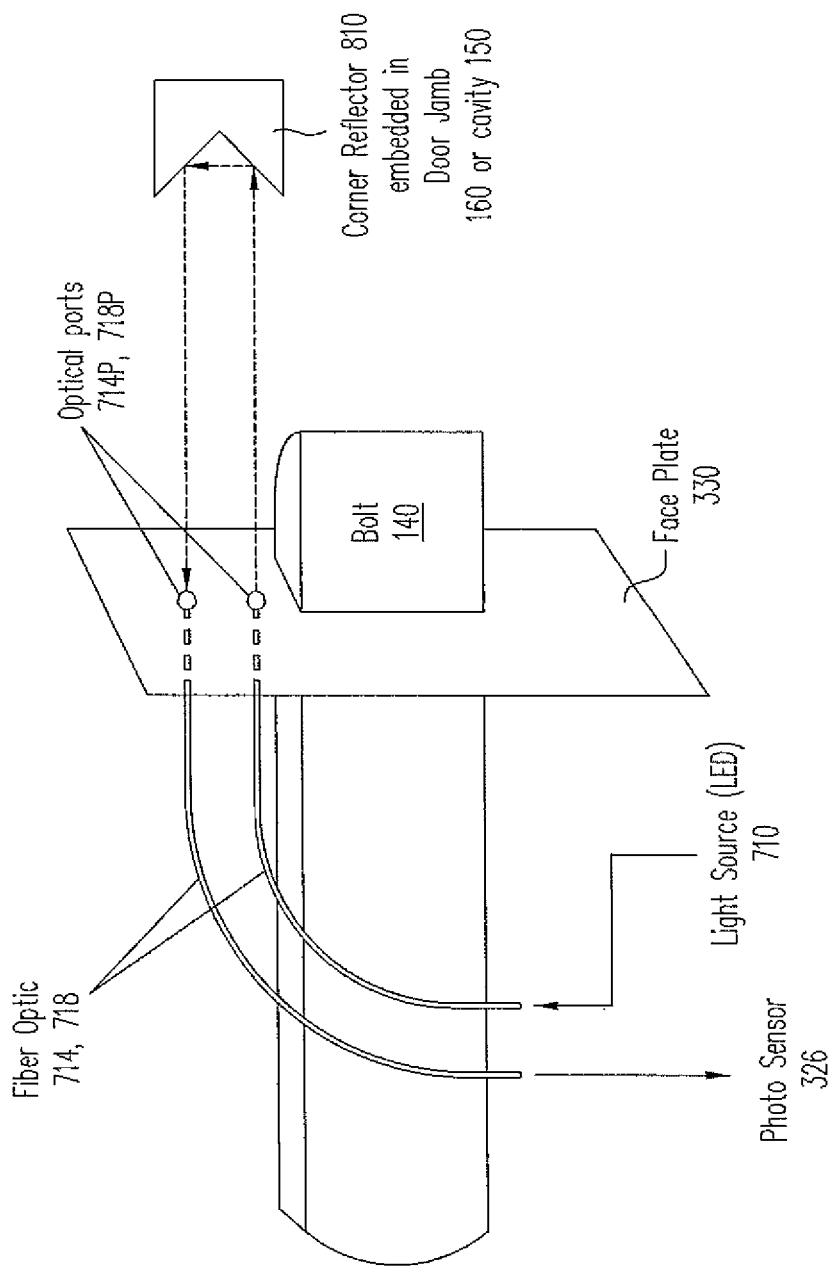
FIG. 9 is a schematic side view of an optical sensing system that senses alignment between a bolt and a door cavity according to some embodiments of the present invention.

The embodiment of FIG. 9 is identical to that of FIG. 7 except that the optical ports 714P, 718P are located on face plate 330 near bolt 140 (similarly to FIG. 8B). Corner reflector 810 can be mounted in cavity 150 or on door jamb 160 or strike plate 340. As in other embodiments described above, one or both of light source 710 and sensor 326 can be mounted directly on face plate 330, and the waveguides can be omitted.

Individual features of FIGS. 7, 8A, 8B, 9 can be combined. For example, output port 714P can be on bolt 140 as in FIG. 7 while but input port 718P can be as in FIG. 9. Alternatively, waveguide 714 can be as in FIG. 7, but sensor 326 can be installed on bolt 140 and waveguide 718 can be omitted. Light source 710, sensor 326, waveguides 714 and 718, and reflectors 810 can be mounted on any part of the lock and the door jamb. For example, light source 710 can be in the lock as in FIGS. 7-9 and light sensor 326 can be in cavity 150, so that no reflector is needed. In such embodiments, the sensor's output signal can be processed by circuitry outside lock 130, and/or can be wirelessly transmitted to computer 318. Also, light source 710 can be located in door jamb 160 and light sensor 326 can be in lock 130, or both can be located in the door jamb but the reflector can be in lock 130. The reflector system may include parts located in lock 130 and may include other parts in or near cavity 150.

Figure 10:
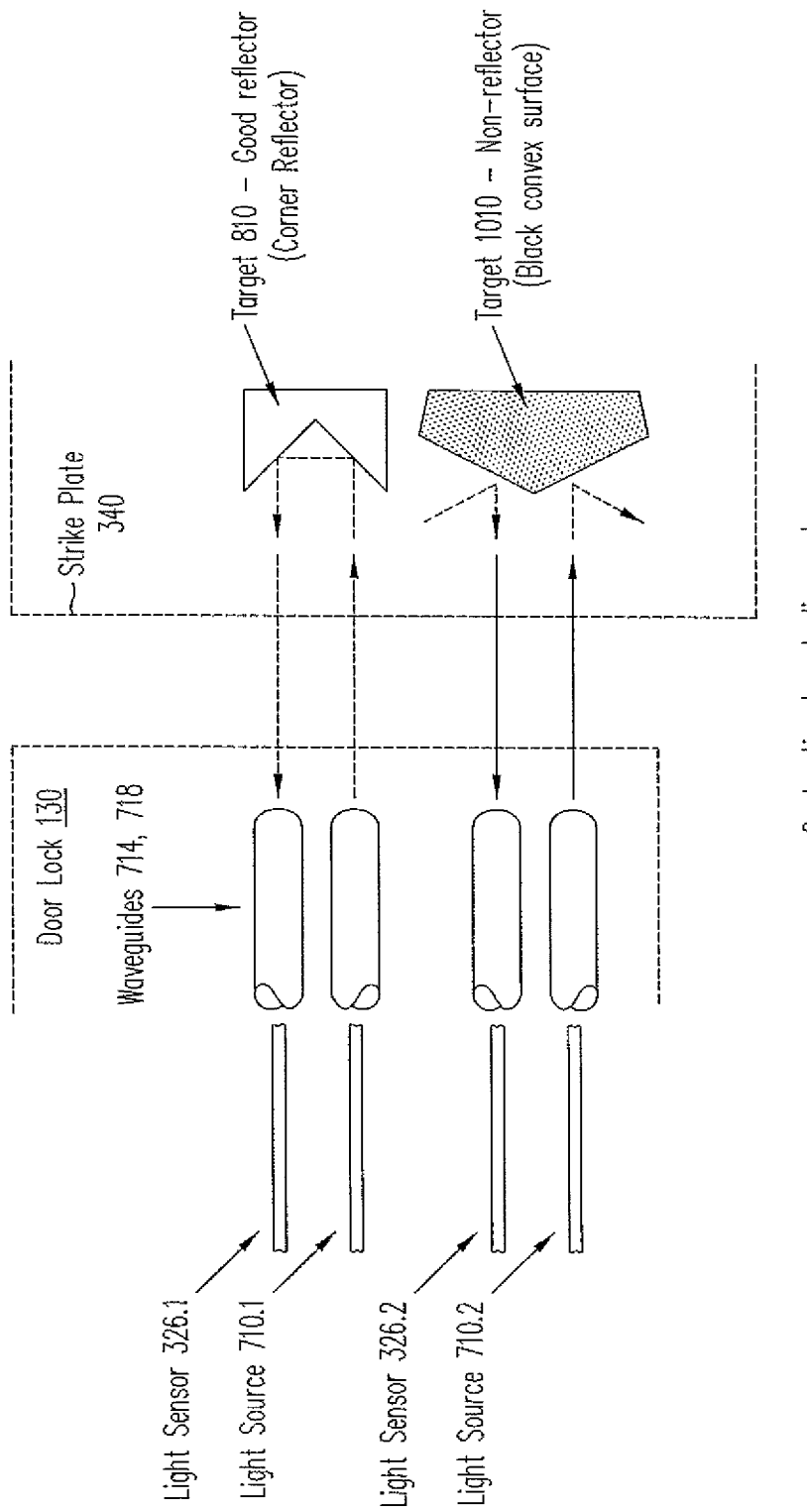
FIGS. 10-18 are schematic illustrations of optical sensing systems that sense alignment between a bolt and a door cavity according to some embodiments of the present invention.

FIG. 10 is a conceptual illustration of an embodiment less vulnerable to false alignment indication such as may occur when a person wearing white clothes walks past the lock 130. This embodiment includes two source/sensor pairs 710, 326. One pair is light source 710.1 and sensor 326.1. The other pair is light source 710.2 and 326.2. Source/sensor pair 710.1/326.1 can be as described above in connection with FIGS. 7-9, and this pair is optically coupled to a reflector 810 ("Target 810") as described above. The source/sensor pair 710.2/326.2 is coupled to a light-suppression target 1010 which absorb or disperses the light from sensor 710.2 and/or reflects the light away from sensor 326.2 when the bolt is aligned with the cavity. For example, target 1010 can be a black convex piece. Source/sensor pair 710.2/326.2 and the target 1010 can be positioned relative to each other and the lock and the door in the same manner as described for respective elements 710/326/810 of FIGS. 7-9. In the aligned state, the light emitted by source 710.2 impinges on target 1010 so that little or no light is received by sensor 326.2. The aligned state is recognized by computer 318 when sensor 326.1 detects reflected light at a level above some energy threshold, and sensor 326.2 detects below some threshold. Suitable threshold depend on many factors (e.g. ambient light) and can be experimentally determined. Alternatively, the computer 318 may detect the aligned state when the amount of light detected by sensor 326.1 increases while the amount of light detected by sensor 326.2 decreases. Both sensors may detect light in both the aligned state and a non-aligned state, but sensor 326.1 detects more of the reflected light in the aligned state than not in the aligned state, and sensor 326.2 detects less of the reflected light in the aligned state than not in the aligned state. The sizes of targets 810 and 1010 are chosen for desired positional accuracy. In the embodiment of FIGS. 7-10, target 810 can be surrounded by complimentary light absorbing material to provide high contrast. In FIG. 10, target 1010 can be surrounded by complimentary reflective material to provide high contrast.

Figure 11:
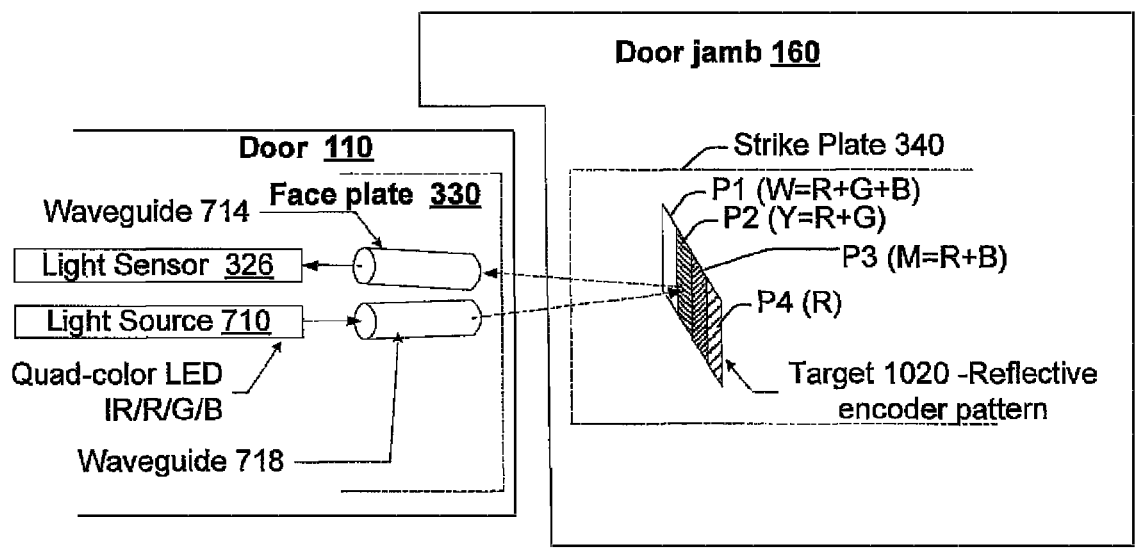
Figure 12:
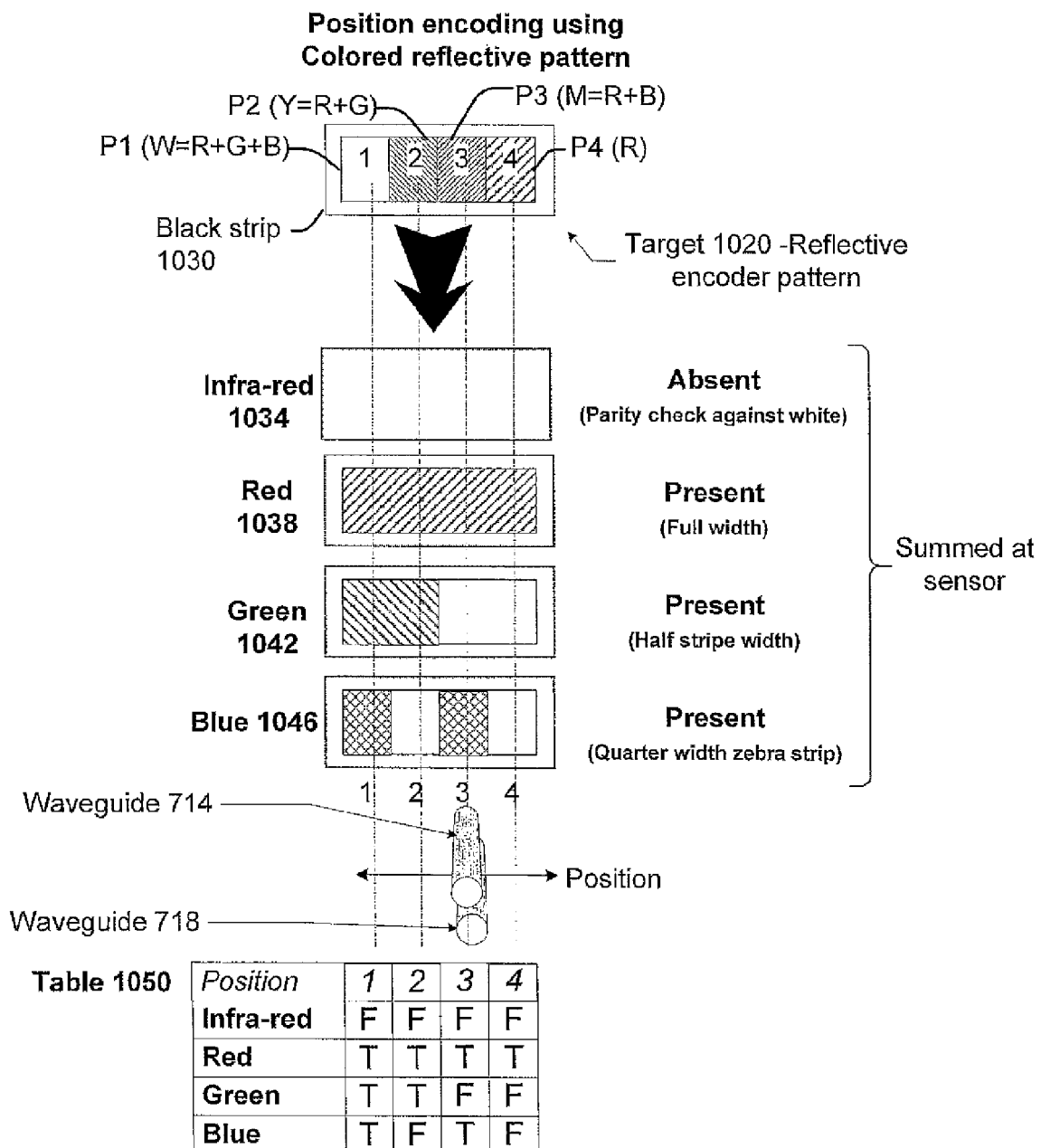

Targets 810 and 1010 can be merged into a single target which includes portions of different reflective/absorptive properties. For example, the target can be colored to provide color encoding which differentiates between the door positions at and near the aligned state. Such color encoding can be used to teach (calibrate) the lock for the aligned state. For example, FIG. 11 illustrates a target 1020 mounted in door jamb 160 (possibly in strike plate 340) with four portions ("bands") P1 (white), P2 (yellow), P3 (magenta) and P4 (red). Light source 710 (e.g. four light sources, possibly light-emitting diodes) emits light having a four-frequency spectrum of IR (infrared), R (red), G (green), and B (blue). Each of portions P1-P4 reflects one of more of these frequencies. Thus, P1 (white) reflects only the red, green and blue; P2 (yellow) reflects only the read and green; P3 (magenta) reflects only the red and blue; P4 (red) reflects only the red. None of portions P1-P4 reflects the infrared. For better contrast, the four portions are surrounded by a black or white strip (i.e. absorbing or reflecting all the four colors), not shown in FIG. 11 but shown at 1030 in FIG. 12. Light source 710 emits white light containing the IR, Red, Green and Blue frequencies, or consists of separate beams for separate frequencies or separate mixes of frequencies, e.g. one beam with mixed IR and Red frequencies and another beam of mixed Green and Blue frequencies. In this embodiment, sensor 326 generates a binary signal (True or False) for each of the four color components IR, Red, Green and Blue as shown in FIG. 12 (in a non-limiting example, the sensor 326 includes four sensors responsive respectively to the IR, Red, Green and Blue frequencies). The sensor signal is thus a 4-bit signal. In some embodiments, light source 710 includes four individually controlled light sources (e.g. LEDs), and in particular a red source, a green source, a blue source, and an IR source. The four sources are turned on and off in sequence and reflection (the sensor signal) is measured to determine which of bands P1-P4 is seen by the sensor. The sensor does not produce a separate signal for each color but produces a signal representing the intensity of light in a broad frequency band including the red, green, blue and IR frequencies. The band seen by the sensor is the band whose color is the color of the LED being on when the sensor senses high light intensity.

The output beam of source 710 has a narrow spacial distribution so as not to overlap adjacent bands at the same time. In some embodiments, however, a wider spacial distribution is acceptable as the sensor can report the light strength at different frequencies to allow blind source separation. The invention is not limited to particular structure or operation of light source 710 or sensor 326.

The sensor and/or computer 318 obtain a 4-bit information signal indicative of the sensed light. The four binary components are shown in table 1050 at the bottom of FIG. 12 for each of the four positions P1-P4 (marked as 1-4 in the table). When the sensor receives light from any one of portions P1-P4, then the IR component is absent (as shown at 1034), and hence the IR signal component is False for each of the four positions as shown in table 1050. The Red component is present in each of portions P1-P4 as shown at 1038; therefore, the Red signal is always True in table 1050. The Green component is present only in portions P1 and P2 as shown at 1042; therefore, the Green signal is True only for these portions in table 1050. The Blue component is present only in P1 and P3 as shown at 1046; therefore the Blue signal is True only for these portions in table 1050.

The IR frequency is provided in light source 710 in order to prevent false alignment indication when the output beam of light source 710 is reflected by a reflective surface located away from the door jamb.

When the lock is installed, the door is manually aligned with the cavity, and the sensor signal in the aligned state is recorded by computer 318 in memory 317. The recorded 4-bit signal consists of the four binary signals IR, Red, Green and Blue in a single column of Table 1050. For example, if the light beam is in portion P2 in the aligned state, then the recorded 4-bit signal is IR=False, Red=True, Green=True, Blue=False. In subsequent operation the computer 318 compares the current 4-bit sensor signal with the recorded signal in memory 317 to detect the aligned state.

If bolt 140 is narrower than cavity 150, then the alignment may be present at different door positions (e.g. both in P2 and P3), i.e. the door may be slightly movable even when locked. Therefore, at the time of calibration, when the door is manually aligned with the cavity, the door can be manually moved in the aligned state, and multiple 4-bit signals from sensor 326 may be recorded in memory 317. In subsequent operation, the computer 318 assumes the aligned state when the current sensor signal is equal to any one of the recorded 4-bit signals in memory 317.

As seen in Table 1050 (FIG. 12), the door position can be obtained just from the Green and Blue components of the reflected light because the Green/Blue combination is unique for each band (T/T for band P1, T/F for P2, F/T for P3, and F/F for P4). This is because each band's color includes a unique combination of the Blue and Green colors (both Blue and Green are present in P1, only Green in P2, only Blue in P3, and neither in P4). This scheme can be extended to position encoding with any number of colors. The word "color" is used herein to identify a spectral power distribution which may include visible or invisible frequencies. In particular, a sensor may identify, and distinguish between (at least up to a multiplicative factor), different spectral power distributions that are metamers (i.e. corresponding to the same color in human visual perception). In FIG. 12, each of Red, Green, Blue and IR is a predefined frequency band.

Suppose now that it is desired to determine a position of any object with respect to another object using some number "n" of non-overlapping frequency bands ("colors") C1, . . . , Cn. One of the two objects ("first object") includes a light source 710 and a sensor 326 as described above, and the other object ("second object") includes a number of portions P1, . . . , PN where N can be any number between 2 and $2^n$ inclusive. The portions P1, . . . , PN can be arranged along a single dimension as in FIGS. 11-12, or in a two-dimensional or three-dimensional pattern (e.g. for position recognition by a robot as the first object). Each portion Pi (i=1, . . . , N) is reflective in a unique set of one or more of the frequency bands C1, . . . , Cn. For example, the portion P1 may reflect in C1 and C2 and absorb in all of C3 through Cn; the portion P2 may reflect in C1 and C5 and absorb in all the other frequency bands; etc. If light source 710 and the sensor system (i.e. sensor 326 and the sensor's signal processor such as computer) operate so that the sensor system identifies which of the frequency bands C1, . . . , Cn are seen by the sensor, then the sensor system identifies the respective one of portions P1-PN and hence the corresponding position.

The colors C1, . . . , Cn need not be distinct frequency bands. For example, different colors may differ in saturation. In one embodiment, the portions P1, . . . , PN are arranged in a two-dimensional array. In each column, the portions Pi differ only in saturation, i.e. in the amount of white color. In other words, the colors in each column "j" can be represented as $C_j+k_m W$ where Cj is a fixed frequency band, W is a white color (for example, a combination of Red, Green and Blue), and k is a coefficient for row "m", where different rows are associated with different coefficients. The frequency bands $C_j$ can be non-overlapping for different columns. Using this scheme, the sensor can estimate the horizontal and vertical positions along the 2D target (2D label). This is a non-limiting example since one can use a sensor sensing many properties of spectral power distribution to arrive at other embodiments.

Figure 13:
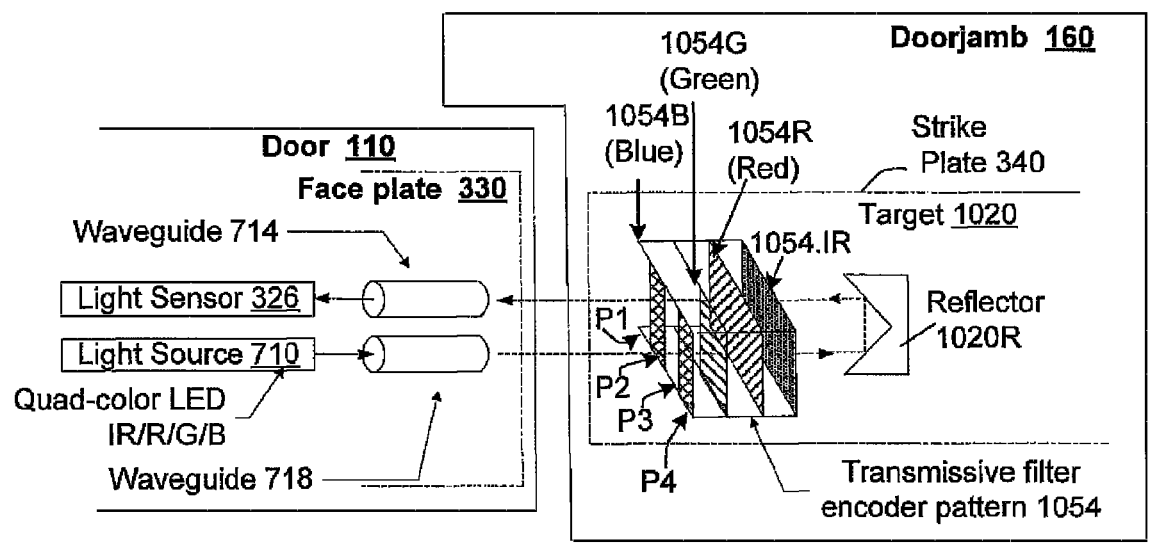

FIG. 13 illustrates a target 1020 with transmissive color filter encoding pattern 1054. The target includes a reflector 1020R (e.g. a corner reflector) which reflects all of the IR, Red, Green and Blue frequencies emitted by light source 710, and may reflect other frequencies. The light source 710 and the sensor 326 can emit and respond to the same frequencies as in FIG. 11. In and near the aligned state, when the output beam from light source 710 impinges on reflector 1020R, the sensor sees the reflected light as coming from one of four adjacent areas (portions) P1, P2, P3, P4 arranged, in the sensor's view, as in FIGS. 11-12. Both the output beam of light source 710 and the reflected beam pass through four transmissive filters 1054B, 1054G, 1054R, 1054.IR mounted on strike plate 340 in front of reflector 1020R. In this example, filter 1054B is blue (subtracts the blue frequency) in portions P2 and P4, and is transparent to all the four frequencies (read, green, blue and IR) in the remaining portions P1 and P3. This is also shown at 1054B in FIG. 14. Filter 1054G is green in P3 and P4 and is transparent to all the four frequencies in P1 and P2. Filter 1054R is red in all the four portions P1-P4. Filter 1054.IR is infra-red (subtracts the red, green and blue) in all the four portions. Alternatively, filter 1054.IR may be transmissive to the red, green, blue and IR in all the four portions, and may be absorptive to some or all frequencies other than the red, green, blue and FR in all the four portions, to help avoid false alignment indication.

Figure 14:
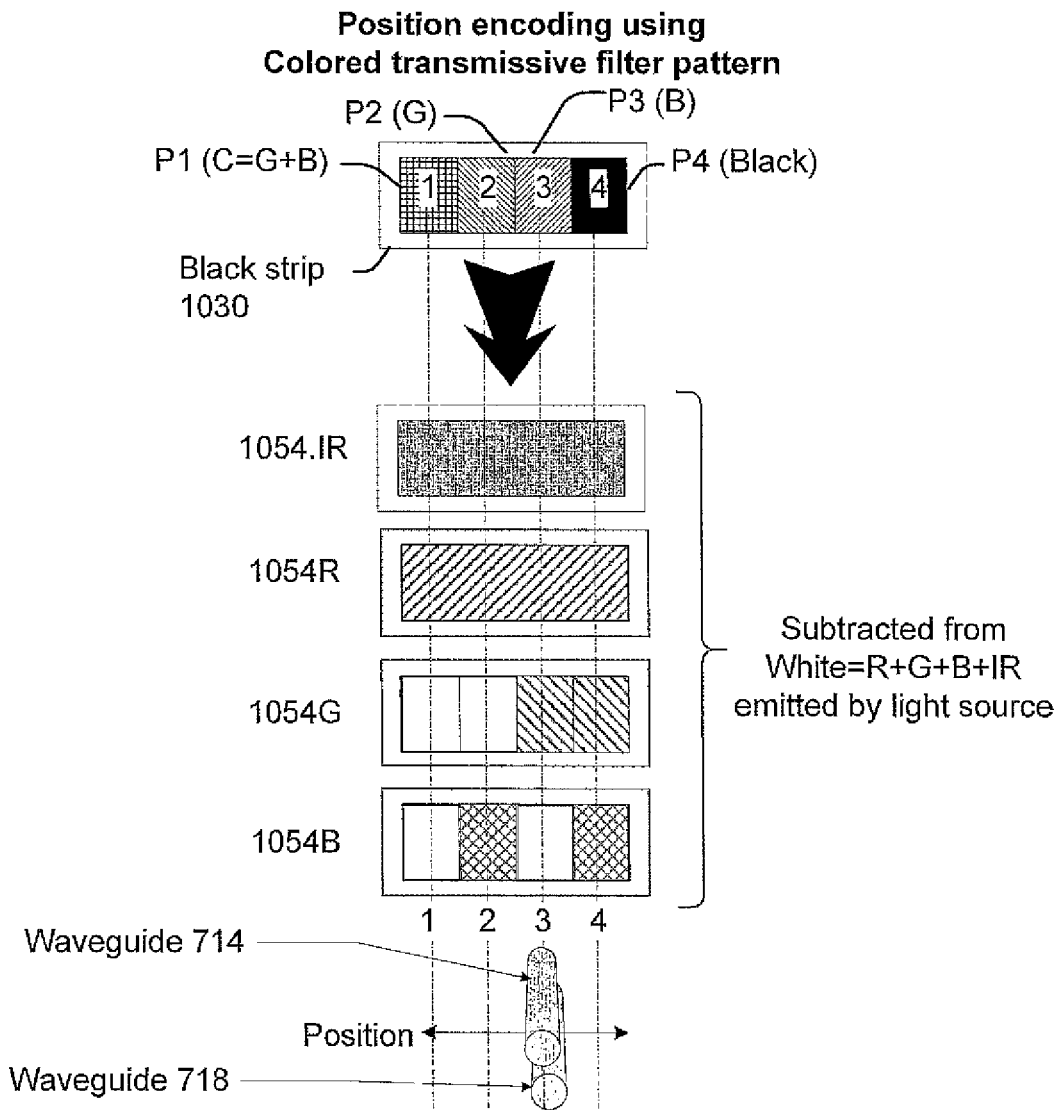

For better contrast, the four portions are surrounded by a black or white strip (i.e. absorbing or reflecting all the four colors), not shown in FIG. 13 but shown at 1030 in FIG. 14.

Sensor 326 generates a binary signal (True or False) for each of the four color components IR, Red, Green and Blue as shown in FIG. 14. The four binary signals are shown in table 1050 at the bottom of FIG. 14 for each of the four portions P1-P4 (marked as 1-4 in the table). When the sensor receives light from any one of portions P1-P4, then the IR and Red components are both absent (subtracted by filters 1054R and 1054.IR), and hence the IR and Red signals are False for the four portions as shown in table 1050. (If the filter 1054.IR is transmissive in all the four portions, then the corresponding line of Table 1050 will be all True instead of False.) The Green component is present only in portions P1 and P2; therefore, the Green signal is True only for these portions in table 1050. The Blue component is present only in P1 and P3; therefore the Blue signal is True only for these portions in table 1050.

The lock is calibrated upon installation as described above for FIGS. 11-12.

The scheme of FIGS. 13-14 can be extended to any 1D, 2D, or 3D position encoding as described above for FIGS. 11-12. More particularly, as seen in Table 1050 of FIG. 14, the door position can be obtained just from the Green and Blue components of the reflected light. Suppose that it is desired to determine a position of any object with respect to another object using some number "n" of non-overlapping frequency bands ("colors") C1, . . . , Cn. One of the two objects ("first object") includes a light source 710 and a sensor 326 as described above, and the other object ("second object") includes a reflector. There can be "n" or more filters placed somewhere into the light path traveled by light between the light source and the reflector when the reflected light is seen by the sensor. The filters, and possibly the light source and the reflector, define a number of portions P1, . . . , PN where N can be any number between 2 and 2n inclusive. The portions P1, . . . , PN can be arranged along a single dimension as in FIGS. 13-14, or in a two-dimensional or three-dimensional pattern (e.g. for position recognition by a robot as the first object). When the light source, the sensor and the reflector are aligned with a portion Pi (i=1, . . . , N), then the sensor sees a unique set of one or more of the frequency bands C1, . . . , Cn. If the sensor system identifies which of the frequency bands C1, . . . , Cn are seen by the sensor, then the sensor system identifies the respective one of portions P1-PN and hence the corresponding position.

The colors C1, . . . , Cn need not be distinct frequency bands, but may differ in saturation or other properties as described above in connection with FIGS. 11-12.

Additional filters (such as 1054.R and 1054.IR) can be provided as a "parity check" to avoid false alignment indication.

In some embodiments, the reflector 1020R is omitted, and light source 710 is placed at the reflector's position in door jamb 160. Filters 1054 may or may not be present. The light source, alone or in conjunction with the filters (if present), provides light beams of four different spectral properties in respective different portions P1-P4. The sensor 326 has a different response to each of these spectral properties to allow the computer 318 to determine whether the sensor is sensing light from one of portions P1-P4 and, if so, from which one. During calibration, the computer records the sensor signal or signals obtained in the aligned state, thus identifying those portions P1-P4 which correspond go the aligned state. During normal operation, the computer recognizes the aligned state when the computer recognizes the sensor signal or signals recorded in the computer memory during calibration.

The invention is not limited to particular colors or the number of colors, to the number of portions P1-PN, and other particulars except as defined by the appended claims. The contrast-improvement area 1030 is optional.

Figure 15:
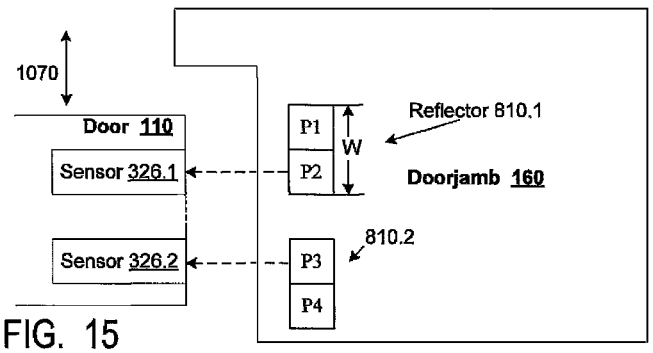

Multiple sensors can be used for calibration purposes with color or black-and-white encoding. FIG. 15 shows schematically the top view of a door 110 with two sensors 326.1, 326.2 and two corresponding reflectors 810.1, 810.2. This is a black-and-white embodiment. The door pivots on hinges (not shown) positioned on the left of the figure, so the door's right edge moves up and down (in the view of FIG. 15) as shown by arrow 1070.

Reflector 810.1 has a top portion P1 and a bottom portion P2. Reflector 810.2 has a top portion P3 and a bottom portion P4. For example, each of P1 and P2 can be one-half of reflector 810.1, and each of P3 and P4 can be one-half of reflector 810.2. If for example each reflector 810 is 2 mm wide (vertical dimension "W" in FIG. 15 is 2 mm), then each of P1-P4 could be 1 mm wide. The dimensions are not limiting as noted above.

Two light sources (not shown) are provided behind the sensors (in the view of FIG. 15) to emit light beams to be reflected by reflectors 810 into the sensors. The light sources and the sensors are mounted on the door (e.g. in face plate 330, not shown), and the reflectors 810 are mounted on the door jamb (e.g. on strike plate 340).

In the state shown in FIG. 15, sensor 326.1 receives reflected light from portion P2, and sensor 326.2 receives reflected light from portion P3. Each sensor generates a binary signal which indicates either reflection ("ON") or no reflection ("OFF"). In FIG. 15, both sensors generate the ON signal.

Figure 16:
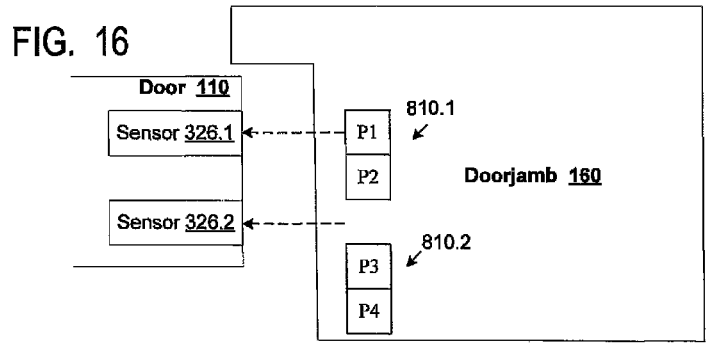
Figure 17:
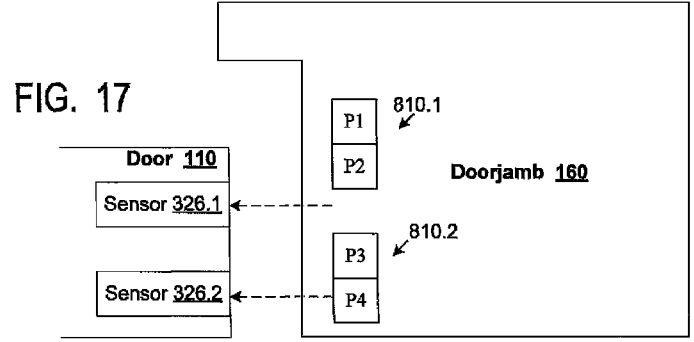

In FIG. 16, the door has moved up a bit (say by 1 mm with the exemplary dimensions given above), so the signal from sensor 326.1 is ON due to reflection from portion P1, but the signal from sensor 326.2 is OFF. In FIG. 17, the door has moved down (say by 1 mm) from the position of FIG. 15, so the signal from sensor 326.1 is OFF while the signal from sensor 326.2 is ON due to reflection from portion P4. The two signals from sensors 326.1, 326.2 together provide four possible states to computer 318:

| Sensor 326.1 signal | Sensor 326.2 signal |
|---|---|
| ON | ON |
| ON | OFF |
| OFF | ON |
| OFF | OFF |

The first three of these states may indicate the aligned state. Upon the lock installation, the door is manually aligned with the cavity, and all of the one or more ON/OFF combinations (2-bit combinations) achieved in the aligned condition are recorded by computer 318 in memory 317. In subsequent operation, the computer 318 assumes the aligned state if the sensor signals are as in one of the recorded combinations in memory 317.

More than two sensors and other reflector patterns can be provided to provide more signal combinations for finer sensing of the door position at or near the aligned state.

The positions of the sensors, light sources, and reflective or light-suppressing targets are interchangeable. For example, in FIG. 10, the targets 810 and 1010 can be positioned on door 110 adjacent to the bolt, and the light sources 710 and the sensors 326 can be on strike plate 340. The techniques of FIGS. 10-17 can be combined with other alignment sensing techniques described above and below.

Figure 18:
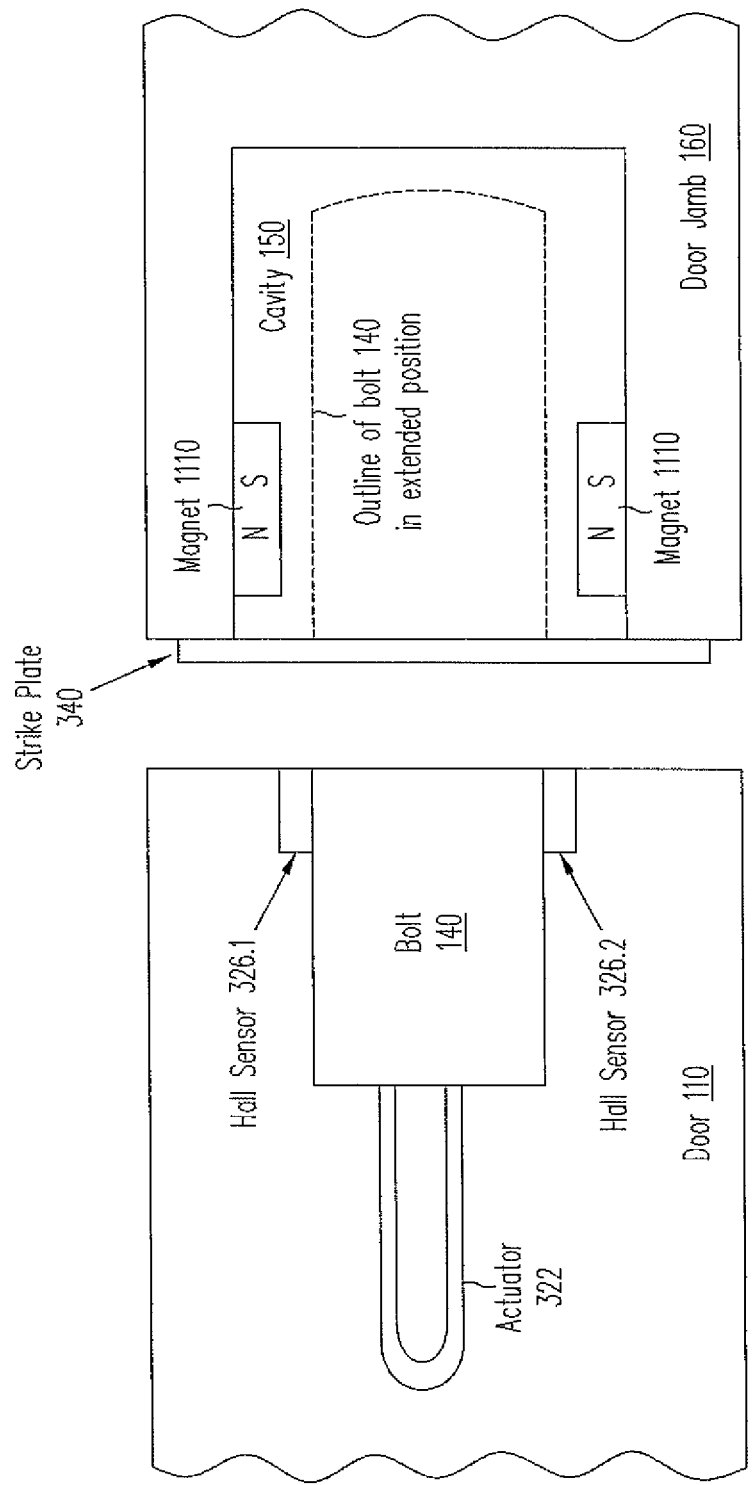

Instead of, or in addition to, the alignment sensing techniques of FIGS. 7-17, magnetic field sensing can be provided as in FIG. 18 for example. One or more magnets 1110 are installed in cavity 150 as in FIG. 18, or on strike plate 340 near the cavity. (Instead of, or in addition to, discrete magnets 1110, one or more magnets can be provided by the strike plate 340 that can incorporate (or be made of) high-coercivity magnetic material magnetized to act as a permanent magnet or magnets.) One or more magnetic sensors 326 (Hall-effect sensors for example) are installed adjacent to bolt 140, or in bolt 140, to measure the strength and/or polarity of the magnetic field of magnets 1110. A signal or signals from sensors 326 indicate to computer 318 when the bolt 140 is aligned with cavity 150.

It will be clear to a person skilled in the art that if magnetic sensing is used, then those parts which are not involved in the magnetic sensing should be made of materials that do not unduly interfere with the magnetic sensing. For example, in some embodiments, bolt 140 and strike plate 340 and face plate 330 are made of non-magnetic or even non-magnetizable materials.

FIG. 18 shows two magnets 1110 each of which has its north pole (N) near the entrance of cavity 150 and the south pole (S) farther from the cavity entrance than the north pole. Other pole arrangements are also possible, e.g. both magnets 1110 may have the south pole closer to the cavity entrance than the north pole. Alternatively, one or more of the magnets may have the north pole closer to the cavity entrance than the south pole, and one or more other magnets may have the south pole closer to the cavity entrance than the north pole. Also, one or more magnets may each have the north and south poles at the same distance from the cavity entrance. One or more magnets can be composite magnets.

In FIG. 18, sensors 326 are Hall-effect sensors (also called "Hall sensors") that are well known transducers whose output voltage (or current) varies in response to changes in magnetic field. They are used for proximity switching, positioning, speed detection, and current sensing. Hall sensors of different types can be combined to provide different alignment-indication signals for more reliable alignment detection. The signals may be interpreted by computer 318 to signal alignment when different types of Hall sensors indicate alignment, or when one or more of different types of sensors indicate alignment. For example, one can:

(a) combine Hall-effect sensors having analog output with Hall-effect sensors having digital (binary) output (i.e. with Hall effect switches) to provide both analog and digital alignment-indication signals;

b) combine Hall-effect sensors that are polar with those that are bipolar (i.e. insensitive to direction of the magnetic flux).

A single type of Hall sensors can also be used.

Some embodiments take advantage of Hall-effect sensors with analog connection to computer 318 to provide flexible capabilities. Examples are:

a) Teaching: For a given lock 130, the sensor threshold can be adjusted (calibrated) for detecting desired alignment. This allows relaxed tolerances on door and lock parts, manufacturing, and installation.

b) Adaptive threshold adjustment.

c) Self monitoring, self-test and e-Diagnostics.

The alignment sensing according to the present invention is not limited to Hall-effect sensors as other types of magnetic sensors can also be used.

The alignment sensing techniques described above can be used both with spring bolts and deadbolts 140 and possibly other kinds of fasteners.

Sensing the Locked or Unlocked State

Sensing whether or not the door is locked is useful for many purposes such as detecting malfunction or unauthorized entry, determining whether or not the bolt should be driven to lock or unlock the door, or others. Prior techniques for sensing whether or not the door is locked are described in the aforementioned U.S. patent application no. 11/867,017 (published as no. 2009/0090148) and U.S. Pat. No. 6,441,735.

Figure 19:
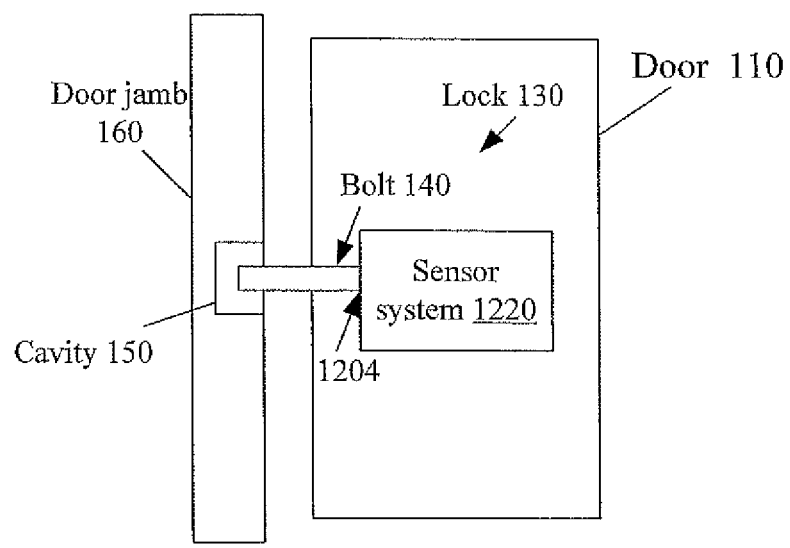
FIG. 19 is a schematic block-diagrammatic side view of a system which senses a bolt state according to some embodiments of the present invention.

In some embodiments of the present invention, the locked or unlocked state is determined using a sensor system spaced from the door jamb, e.g. at bolt end 1204 (FIG. 19) opposite from the door jamb. A suitable sensor system 1220 can be located at end 1204 or between end 1204 and the door jamb.

Figure 20:
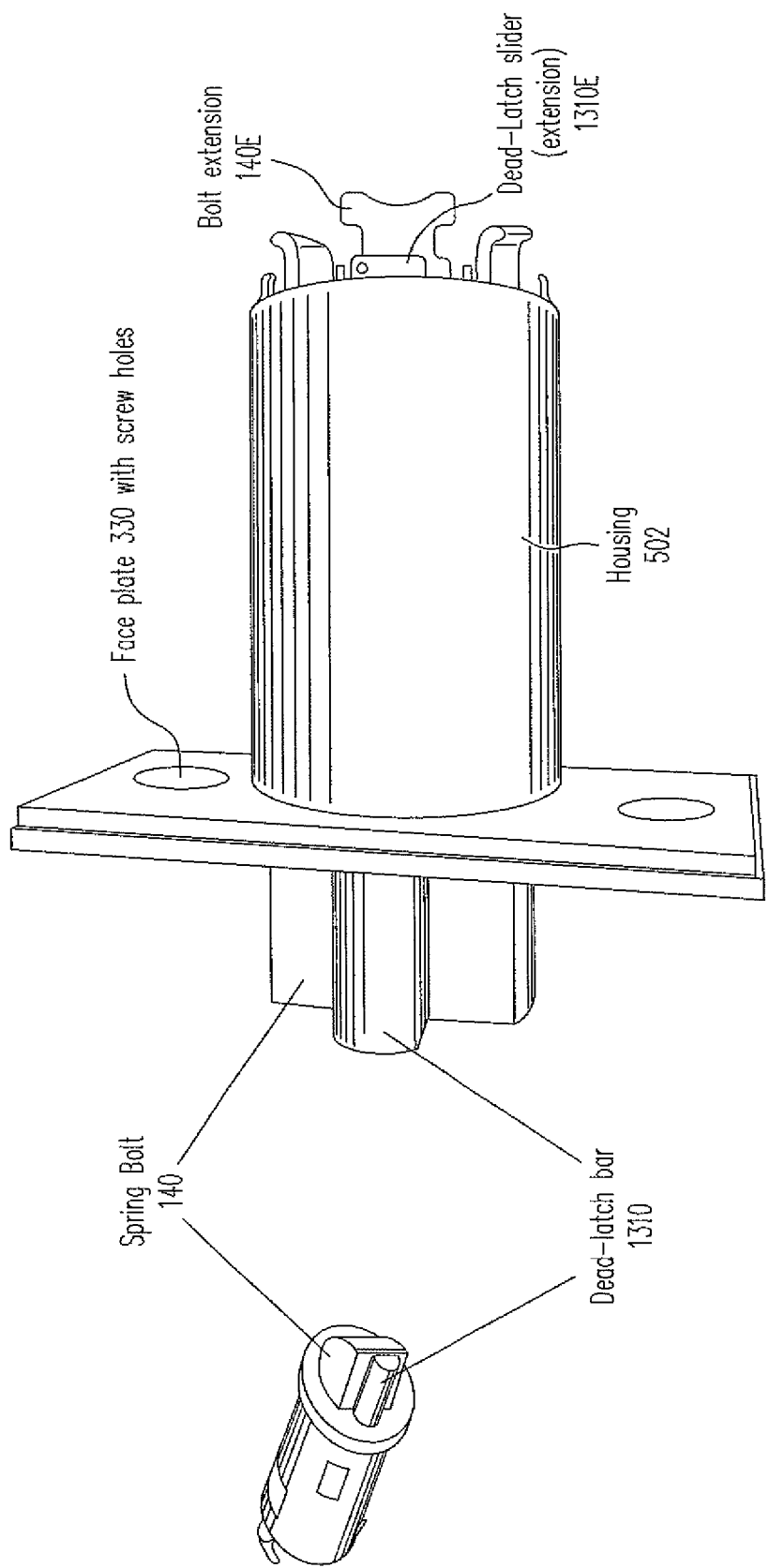
FIG. 20 presents perspective and schematic views of a dead latch used in prior art and also used in some embodiments of the present invention.

In some embodiments, sensor system 1220 is inside the lock's housing 304 (FIG. 3) and thus is protected by the housing. Some embodiments are used with spring bolts, other embodiments are used with deadbolts, and exemplary embodiments will now be described on the example of a dead latch (FIG. 20). The dead latch is a spring latch strengthened against lock-picking. More particularly, in addition to spring bolt 140, the dead latch includes a spring-loaded dead-latch bar ("DL-Bar") 1310 mounted in the door if bolt 140 is in the door. If the bolt is in the door frame, then DL bar 1310 can also be in the door frame. Other locations may also be possible, but they are such as to enable interlocking (coordinating) the bolt with the DL-bar as described below. Bolt 140 and DE-bar 1310 can both be extended or retracted. However, if bolt 140 extended when DL-bar 1310 is retracted, the retracted DL-bar does not allow bolt 140 to retract except by operation of actuator 322, e.g. by a mechanical or electronic key or handle (not shown). This configuration—DL-bar 1310 retracted and bolt 140 extended—occurs when the door is being closed. During closing, at first bolt 140 and dead-latch bar 1310 are retracted into common housing 502 by the door jamb or strike plate, but then cavity 150 allows spring bolt 140 to extend. Dead-latch bar 1310 is not provided a cavity or other space to extend into. Consequently, bolt 140 cannot be pushed into the door (cannot be retracted) by fraudulent, lock-picking means such as a thin plastic card, pin or thin metal strip. The lock can still be unlocked by legitimate means such as a key. This coordination between DL-bar 1310 and bolt 140 is sometimes referred to as interlocking.

Sensor system 1220 may sense the position of bolt 140, of dead lock bar 1310, or both. Sensor system 1220 can employ mechanical switches, optical detectors, break-the-beam optical detectors, magnetic sensors, magneto-resistive sensors, and possibly other sensing techniques. FIG. 21 illustrates an embodiment in which the sensor system 1220 includes (i) a magnet 1410 (generating a magnetic field with magnetic field lines 1420), and (ii) a magnetic field sensor 1430. Here the bolt 140 has an extension 140E which protrudes out of housing 502 at back end 1204 and which can be (and typically is) connected to actuator 322 (FIG. 3). Dead latch bar 1310 has an extension 1310E which protrudes out of the housing 502 at back end 1204. Magnet 1410 is installed on DL-bar extension 1310E. Sensor 1430 is installed on the back of housing 502. Magnet 1410 and sensor 1430 are thus both outside the housing. They are not protected by the housing, and this can be a disadvantage. An advantage of this design however is that the magnet 1410 and sensor 1430 are easy to install on existing locks, and sensor 1430 is easily accessible for wired connection to computer 318. Sensor 1430 could be installed instead in space 1434 inside housing 502. The invention is not limited to a particular position of magnets or sensors.

The positions of magnet 1410 and sensor 1430 can be assertive or passive. In the assertive configuration, the sensor senses stronger magnetic field when bolt 140 is extended than when the bolt is retracted. In the passive configuration, the magnetic field sensed by the sensor is stronger when bolt 140 is retracted than when the bolt is extended.

In some embodiments, if DL bar 1310 is retracted as sensed by sensor 1430 while bolt 140 is aligned with the cavity as signaled by alignment sensors such as described above in connection with FIGS. 7-18, then the door is assumed to be locked by computer 318. Otherwise (DL bar 1310 is extended or alignment is not detected), the door is assumed to be unlocked.

In some embodiments, discrete magnet 1410 is omitted, and instead coercive magnetic material is incorporated into dead-latch bar 1310 and/or extension 1310E and is magnetized to become permanent magnet. Non-magnetic sensing can also be used, e.g. optical sensing. A light source and an optical sensor could be positioned to detect movement of bolt 140 and/or DL-bar 1310. In some embodiments, bolt 140 or DL bar 1310 (or one or both of their extensions 140E and 1310E) are used as a flag for break-the-beam sensing. In some embodiments, one or more of such sensing systems (magnetic or optical or others) are provided to sense the position of bolt 140 (by sensing the position of the bolt extension 140E for example) at the lock's end 1204 outside housing 502. In magnetic sensing, a magnet can be replaced by magnetic material in bolt 140.

In some embodiments, sensor system 1220 senses both the position of bolt 140 and the position of DL bar 1310, and if DL bar 1310 is retracted while bolt 140 is extended, this indicates to computer 318 that the door is locked. The alignment sensing may or may not be present and, if present, may or may not be used to determine whether or not the door is locked.

In FIG. 21, numeral 1440 labels a dead-latch interlock mechanism which interlocks DL bar 1310 and bolt 140 when DL bar 1310 is retracted and bolt 140 is extended. This can be a conventional mechanism, and it is shown schematically (conceptually) only.

FIG. 22 shows a similar dead latch but the magnets and the sensors are inside housing 502 to protect them from abusive handling during shipping and installation. Magnet 1410 and sensor 1430 detect the position of DL bar 1310. Magnet 1510 and sensor 1530 detect the position of bolt 140. Magnet 1410 is affixed to the back of DL bar 1310 where the DL bar connects to its extension 1310E. Magnet 1510 is affixed to the back of bolt 140 where the bolt connects to its extension 140E. Sensors 1430, 1530 are inside housing 502 on the housing's back wall. Housing 502 may or may not incorporate (possibly be made of) magnetic material. The choice of the housing material has bearing on the magnetic circuit used for sensorization, and in particular on the magnet and sensor positioning.

The sensing indication by computer 318 can be as described above, i.e. computer 318 may indicate the locked state when bolt 140 is extended and DL-bar 1310 is retracted. Alternatively, the bolt and/or DL-bar position sensing may be combined with the alignment sensing described above to determine whether or not the door is locked. For example, computer 318 may indicate the locked state when bolt 140 is extended and the alignment is sensed (regardless of the DL-bar position), or when bolt 140 is extended and DL-bar 1310 is retracted and the alignment is sensed, or when either bolt 140 is extended or DL-bar 1310 is retracted while the alignment is sensed. Some embodiments do not include an alignment sensing system.

Figure 23:
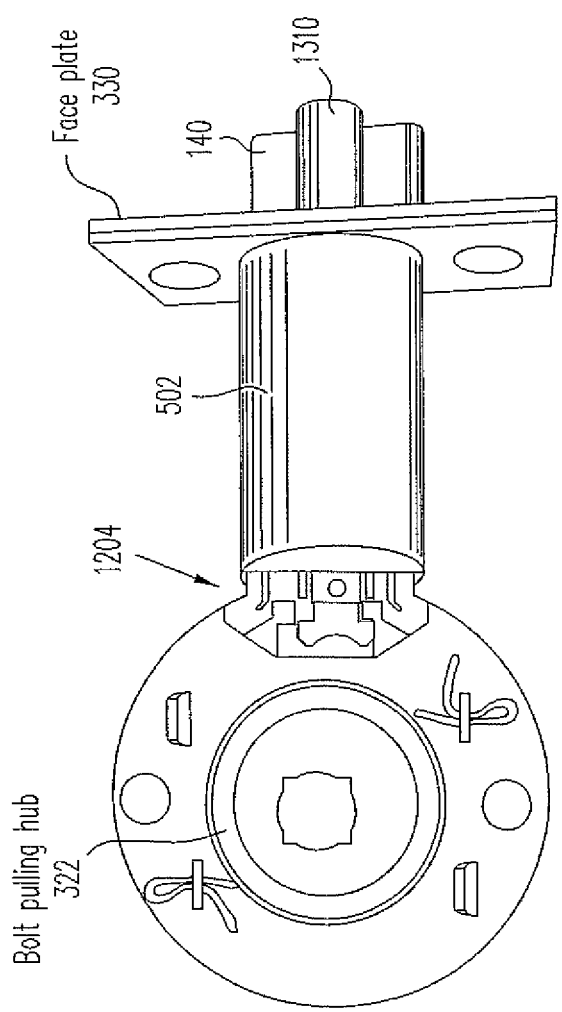
FIG. 23 is a side view of a dead latch attached to a lock hub according to some embodiments of the present invention.

FIG. 23 shows a dead latch according to some embodiments of the present invention, with the back end 1204 attached to a bolt pulling hub 322 which effects actuation to retract the bolt when a handle (not shown) inserted into the hub's center is turned in a predefined direction. Of note, in some electronic-door embodiments, the actuator 322 of FIG. 3 does not itself retract the bolt but allows the bolt to be retracted by turning a knob or a handle when a signal from computer 318 allows unlocking (this signal can be generated by computer 318 in response to a signal received by antenna 310, or in response to reading a magnetic card, or sensing proximity card swipe, or on some other event as appropriate). Such manual unlocking is particularly desirable for power-conscience (e.g. battery operated) locks. In other electronic-door embodiments, the actuator 322 can automatically retract the lock in response to computer 318 signal.

Figure 24:
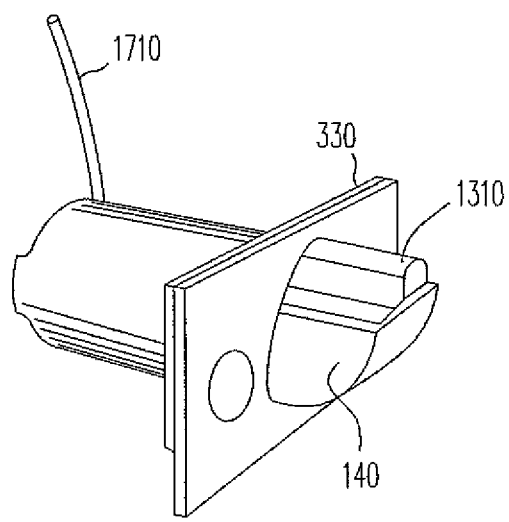
FIGS. 24, 25 are front views of dead latches according to some embodiments of the present invention.
Figure 25:
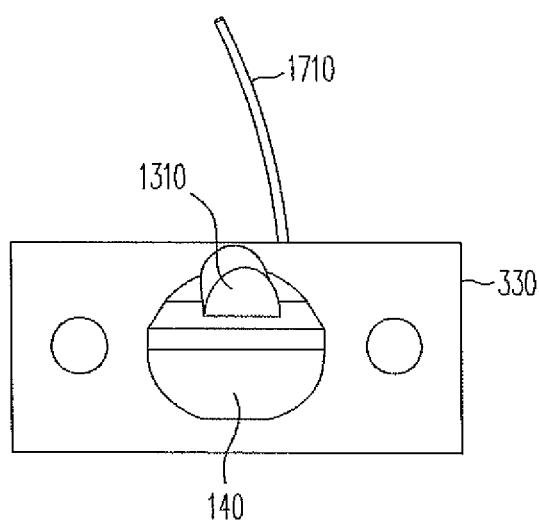
Figure 26:
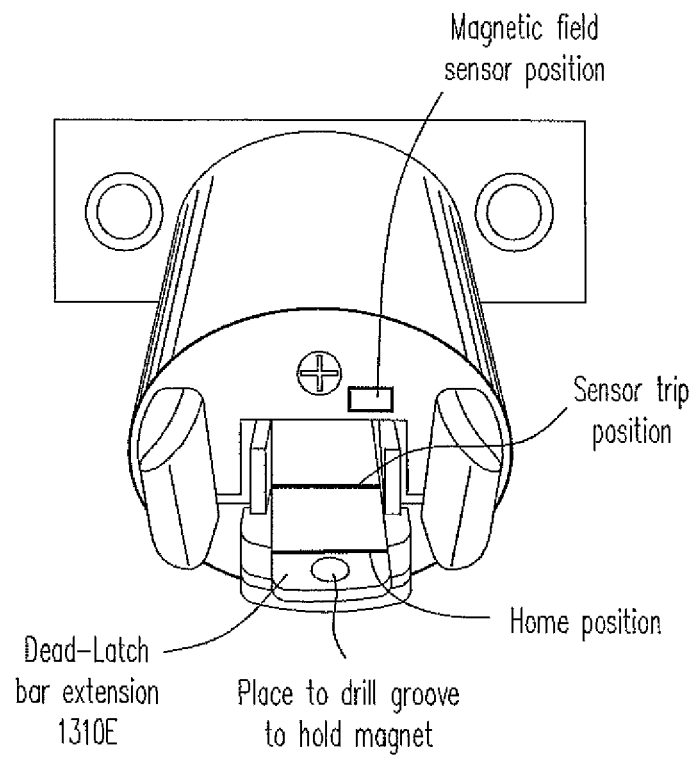

FIG. 24 is a front elevated view of the dead latch; FIG. 25 is a front view. A cable 1710 connects the sensors to computer 318.

Figure 27:
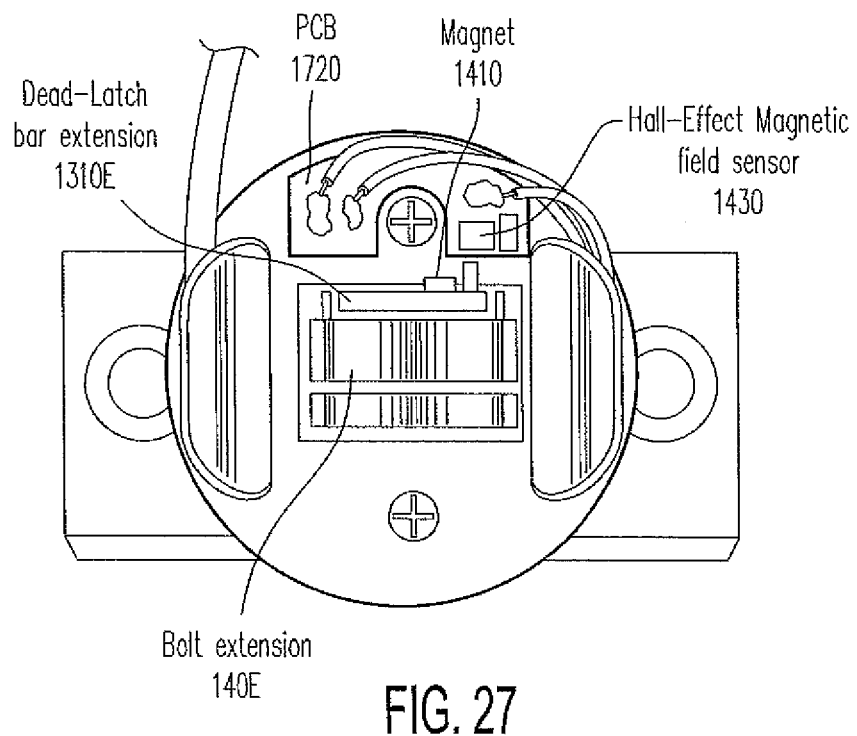
Figure 28D:
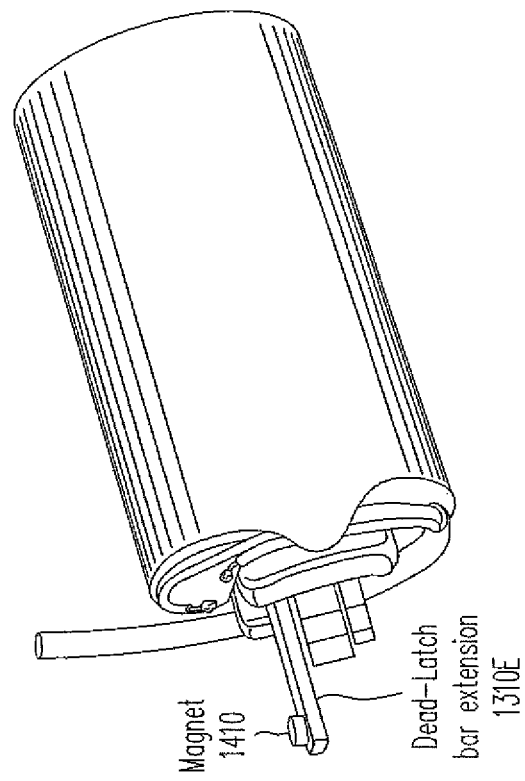
Figure 28C:
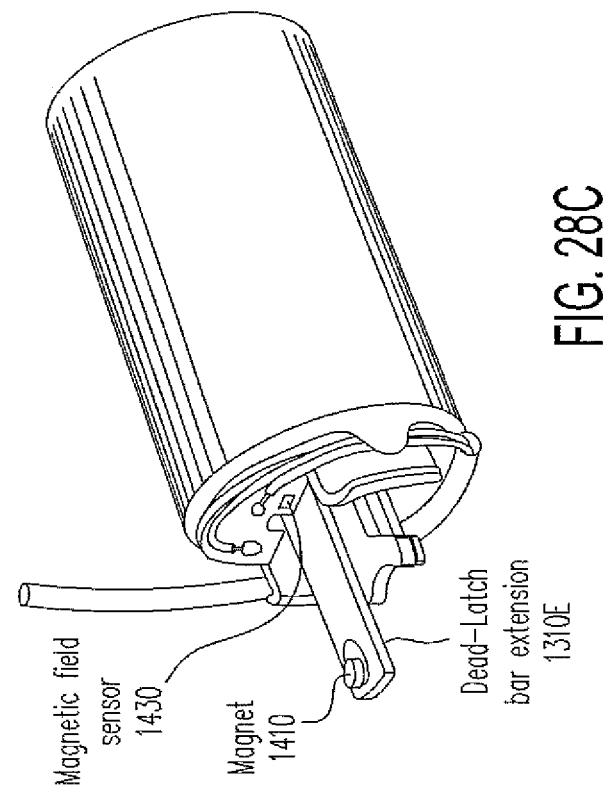

FIGS. 26, 27, 28A, 28B, 28C, 28D all show the dead latch back end 1204 in somewhat different views. These figures show positions of magnets and magnetic sensors for sensing the DL bar position. In FIGS. 28A-28D, bolt 140 is extended and DL bar 1310 is retracted. Printed circuit board (PCB) 1720, shown in FIG. 27, provides circuitry for connecting the sensor 1430 to computer 318.

Figure 29:
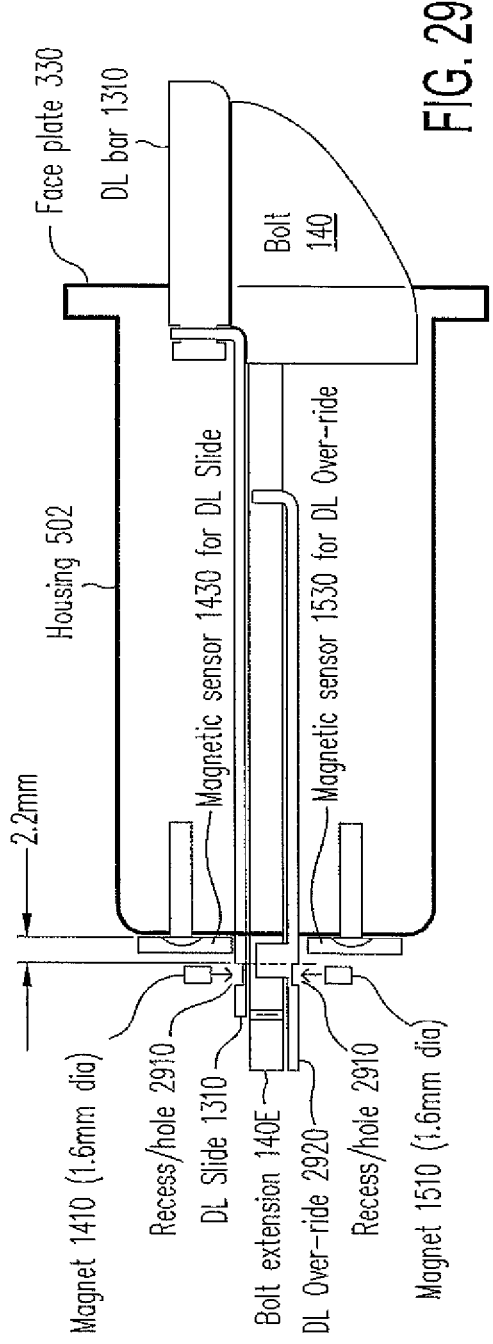
FIGS. 29 and 30 are each a schematic side view of a system which senses the positions of the bolt and/or dead-latch bar according to some embodiments of the present invention.

Extensions 140E, 1310E can be of one-piece construction with bolt 140 or DL bar 1310 respectively, or can be separate pieces rigidly attached to the bolt or the DL bar as shown in FIG. 29. DL bar extension 1310E is sometimes referred to as "DL slide" herein. Further, the magnets and the sensors do not necessarily have to be installed on bolt 140 or DL bar 1310 or their extensions but can be installed in other ways so as to sense the bolt's or DL bar's position. For example, some of the magnets and sensors may be installed on other parts moving with the bolt or the DL-bar so that the magnets' or sensors' position would indicate the bolt or DL-bar position. In FIG. 29, magnet 1410 is installed in a recess 2910 in DL slide 1310E and is used to sense the DL bar position. Magnet 1510 is used to sense the bolt 140 position. Magnet 1510 is not installed on the bolt or its extension but is rather installed on DL override 2920, in a bottom recess 2910 in the DL override. DL override 2920 travels with bolt 140 when the bolt is extended or retracted. DL override 2920 disengages the bolt 140 from DL bar 1310 when the lock is being opened by operation of actuator 322. For example, in some embodiments, when actuator 322 pulls on DL override 2920, then the bolt is retracted irrespective of the DL-bar position.

In FIG. 29, magnet 1410 and magnetic sensor 1430 are positioned similarly to FIG. 21. Magnetic sensor 1530 is positioned on the outside wall of housing 502 to sense the position of magnet 1510. Magnets 1410, 1510 can be outside of housing 502, or can be inside the housing, or one or both of the magnets can be inside the housing when the bolt or DL bar is extended, and can be outside when the bolt or DL bar is retracted.

Figure 30:
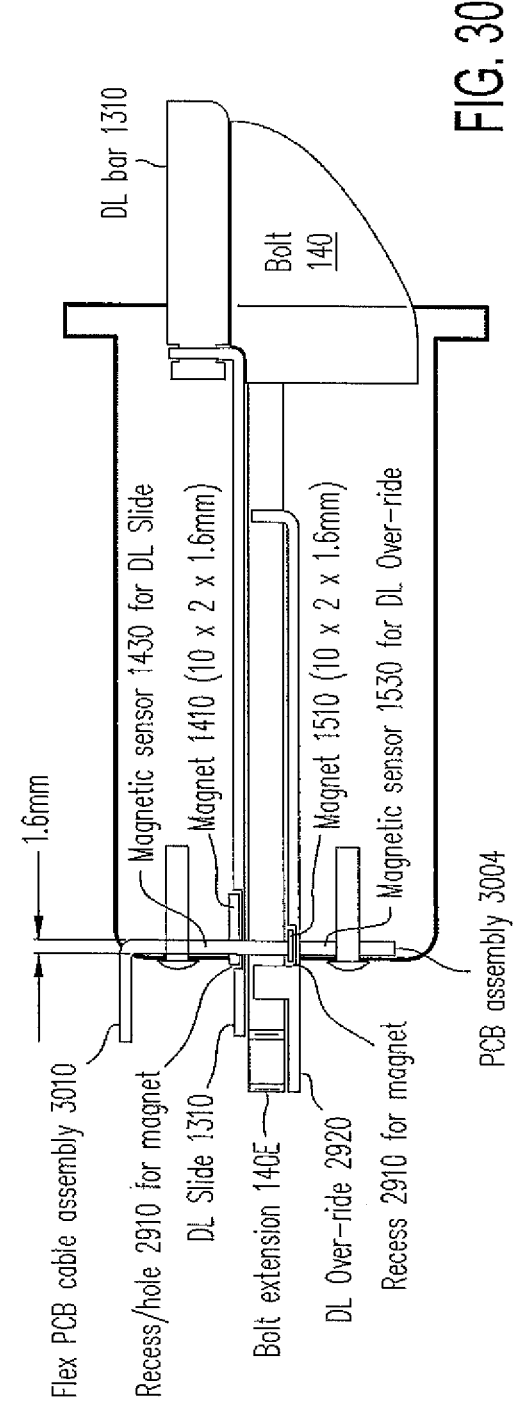

FIG. 30 is similar, and shows in addition a PCB assembly 3004 mounted on the back inside wall of housing 502 to process signals from sensors 1430, 1530 and provide the processed signals to computer 318 via flexible PCB cable assembly 3010. This configuration protects the sensors from abusive handling during shipping and installation. Also, magnet 1510 is installed in a top recess in DL override 2920, not at the bottom of the DL override as in FIG. 29; this arrangement encapsulates the magnet thus increasing mechanical robustness and minimizing mechanical mechanism design change.

Some embodiments include a sensor which does not detect the absolute position of bolt 140 or DL bar 1310 but detects only their relative position. For example, a magnet could be installed on bolt 140 or its extension 140E, and a magnetic sensor could be installed on DL bar extension 1310 or its extension 1310E.

These schemes are exemplary and not limiting. As noted above, all the dimensions are exemplary.

Alignment Assist

In conventional locks, the alignment between bolt 140 and cavity 150 is ensured by simply closing the door. This may work well with a spring bolt due to the spring action extending the bolt when the bolt meets the cavity. However, this does not always works well, as for example when the door sags. With a deadbolt, the bolt can miss the cavity even if the door does not sag, for example if the door stop allows the door to travel past the aligned state, because there is no spring to extend the deadbolt when it meets the cavity.

Figure 31:
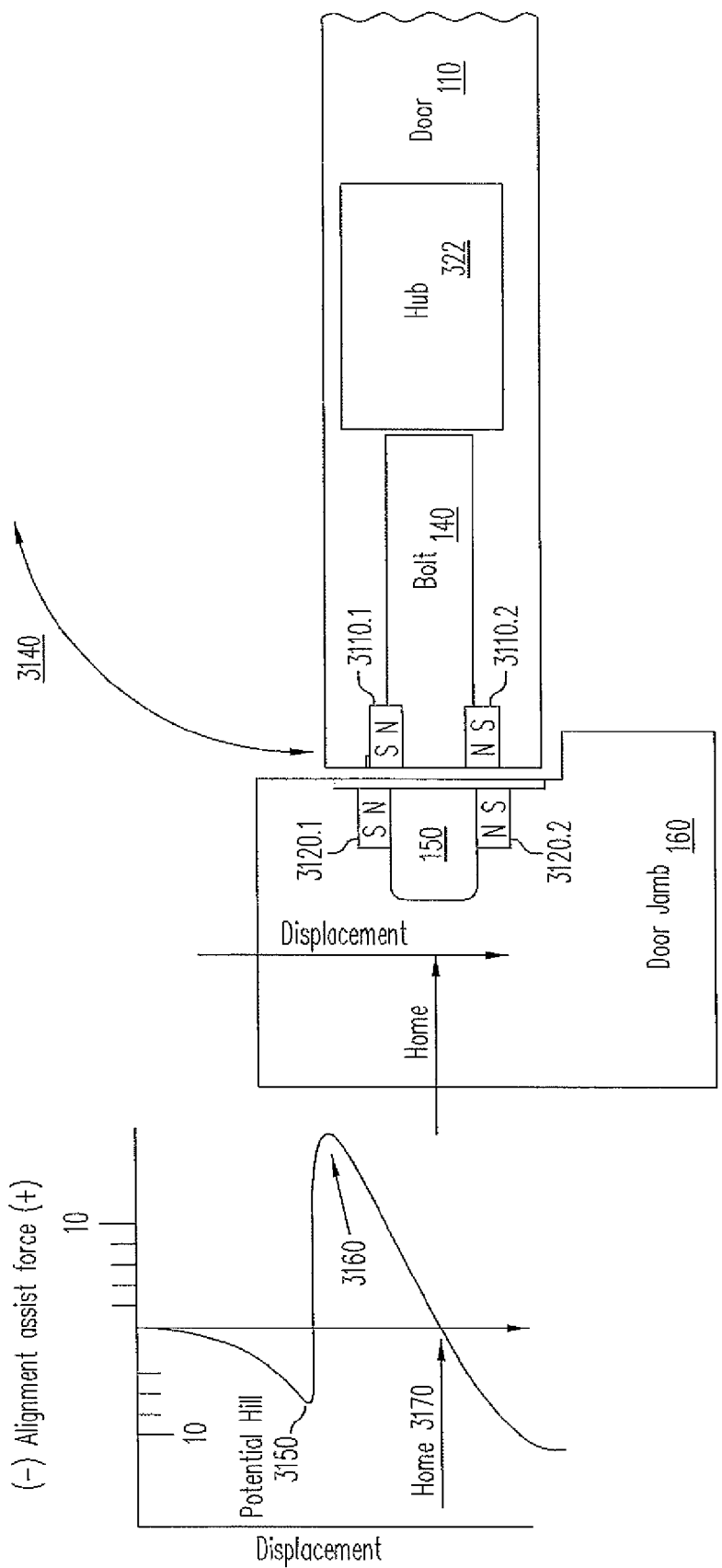
FIG. 31 illustrates a top view and a force/displacement graph of a system for magnetically aligning a bolt with a cavity according to some embodiments of the present invention.

Some embodiments of the present invention provide door-alignment "assist" (assistance) schemes suitable for manual and/or automatic operation. One embodiment is illustrated in FIG. 31 in top view. The door pivots on hinges (not shown) positioned on the right in this view, so the door's left edge rotates clockwise and counterclockwise as shown by arrow 3140. The door is closed in counterclockwise motion. The door stop, made as a protruding portion of door jamb 160, makes it possible for the door's bolt 140 to miss its aligned position with door jamb's cavity 150. The invention is not limited to such features however.

In order to station the door in the aligned position, one or more magnets 3110 (magnets 3110.1 and 3110.2 in FIG. 31) are provided in the lock immediately adjacent to bolt 140, and one or more matching magnets 3120 (two magnets 3120.1 and 3120.2 in FIG. 31) are mounted in or immediately adjacent to cavity 140. In the aligned state and near the aligned state, the magnets 3110 are attracted to magnets 3120. More particularly, each magnet extends left-to-right between its north and south poles. The north poles of magnets 3120 are near the cavity entrance, and the south poles of magnets 3110 are at the door edge. In each magnet pair 3110.$i$, 3120.$i$ ($i=1$ or 2), the distance between the north pole of magnet 3110 and the south pole of magnet 3120 is at its minimum in the aligned state. (This arrangement of the poles is not limiting; for example the north and south poles can be interchanged.)

The magnets are positioned so that near the aligned state the magnets pull the door into the aligned state, and the aligned state is a stable equilibrium, i.e. the magnets resist the door motion out of the aligned state. The aligned state is sometimes referred to as the "home" position. A graph at the left of FIG. 31 shows the alignment assist force (the resultant magnetic force due to magnets 3110, 3120) along the horizontal axis as a function of the door displacement along the vertical axis. When the door moves counterclockwise towards the aligned position, the north pole of magnet 3110.2 approaches the north pole of magnet 3120.1. The resultant force is repelling (shown as negative in the graph at the left), and this repelling force increases and reaches its maximum magnitude at a point shown as 3150 in the graph. This point is the top of a potential hill, similar to spring-and-roller assisted centering devices used in cabinet closets. Up to this point, the magnets resist door closing. Past this point, the magnets assist in the door closing. The resultant assist force increases to its maximum at some point 3160, then decreases to zero at "home" position 3170 in which the bolt is aligned with the cavity (at this point typically the magnets have the greatest attractive force, but the attractive force is in the direction of the door hinge (not shown) thus producing zero torque). At point 3170 the resultant magnetic force resists either clockwise or counterclockwise door motion. This arrangement works well for doors with low to medium friction, but the invention is not limited to such doors.

Some embodiments employ magnetizable material, e.g. soft iron, on one side of the door, instead of magnets 3110 or instead of magnets 3120. For example, one of the strike plate and the face place could be soft iron. There is no repelling force in door closing, similar to embodiments described below in connection with FIG. 35A.

Figure 32A:
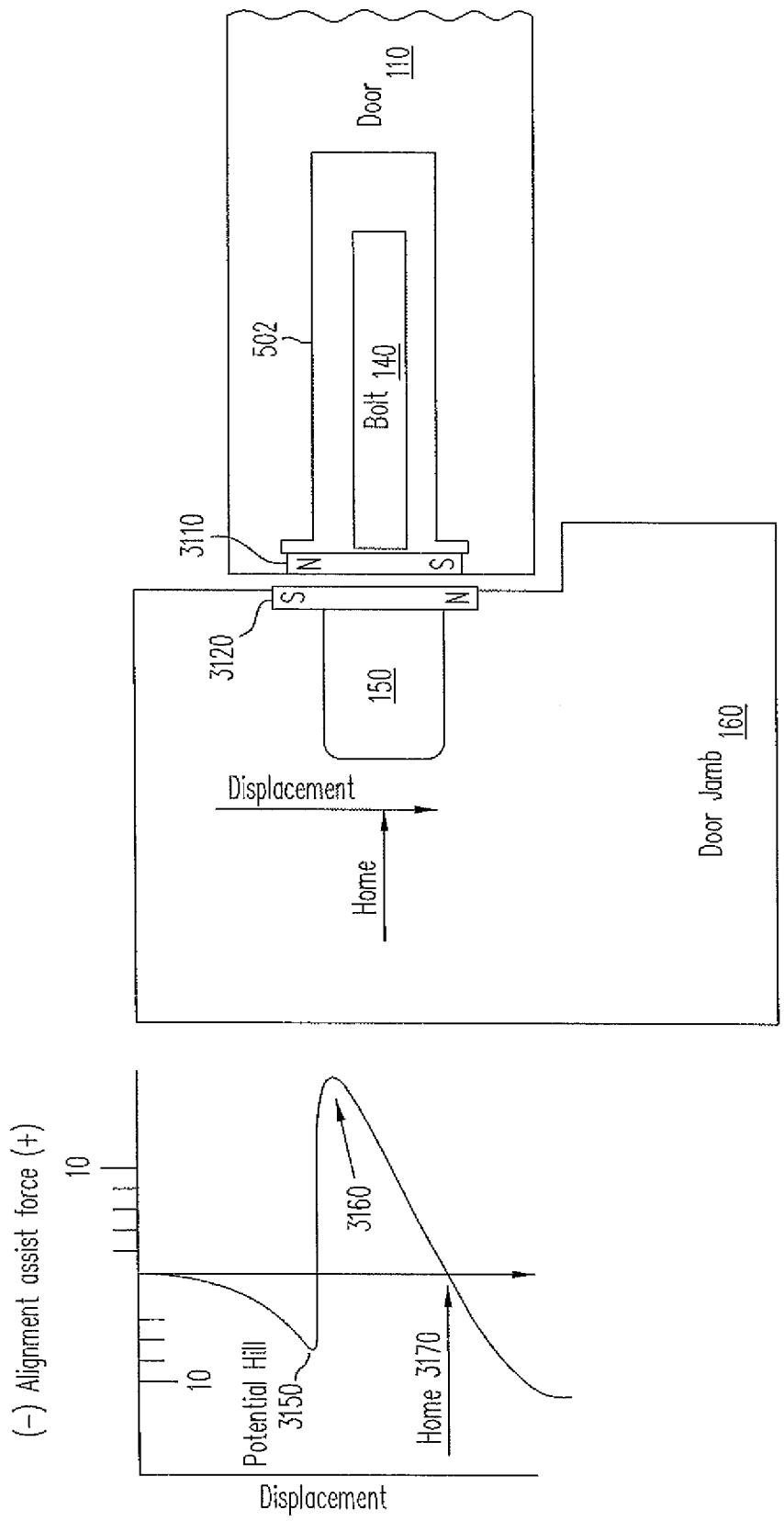
FIG. 32A illustrates a top view and a force/displacement graph of a system for magnetically aligning a bolt with a cavity according to some embodiments of the present invention.

FIGS. 32A (top view) and 32B (side view of door jamb 160 only) illustrate a similar arrangement, but each magnet 3110, 3120 is a bar or strip magnet which extends along the edge of the door or the door jamb, i.e. along the face plate or strike plate respectively, between the magnet's north and south poles. In the aligned ("home") state, the north pole of each of magnets 3110, 3120 is adjacent to the south pole of the other one of the two magnets, and the door is at stable equilibrium as the magnetic force resists the door motion in either clockwise or counterclockwise direction. When the door is being closed, the magnets at first resist the door closing, but then push the door into the aligned state, as in the embodiment of FIG. 31. This is illustrated by the force/displacement graph at the left of FIG. 32A.

Figure 32B:
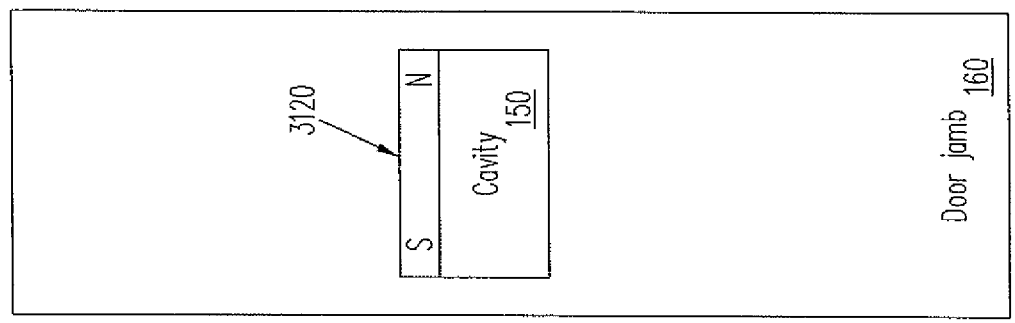
FIG. 32B is a side view of a door jamb of the system of FIG. 32A according to some embodiments of the present invention.

Each of magnets 3110, 3120 can be positioned above the bolt or cavity respectively as in FIG. 32B, or below the bolt or cavity. The magnets can be spaced from the bolt or cavity. Alternatively, the magnet 3120 can be in the cavity or at the top or bottom boundary of the cavity and can be completely or partially within the cavity; magnet 3110 can be in a matching position. The magnets do not have to be at the same height, i.e. in the view of FIG. 32B the magnet 3120 can be higher or lower than the magnet 3110.

In some embodiments, magnet 3120 is the strike plate or part of the strike plate. In some embodiments, magnet 3110 is omitted but the face plate is made from a high coercive force magnetic material. In other embodiments, magnet 3120 is omitted but the strike plate is made of a high coercive force magnetic material magnetized to become a permanent magnet.

Figure 33B:
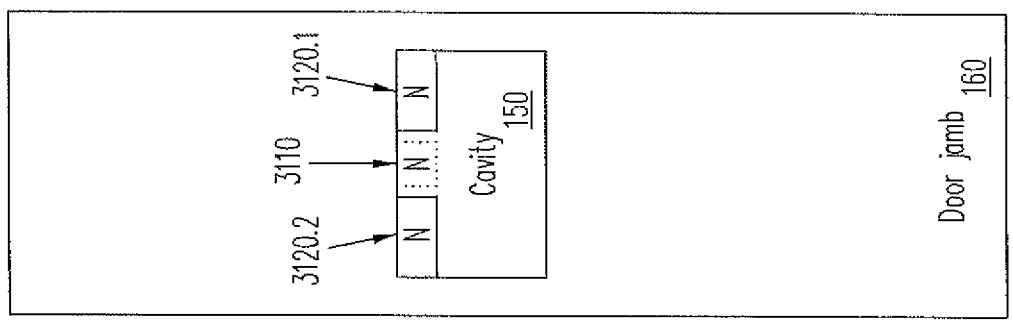
FIG. 33B is a side view of a door jamb of the system of FIG. 33A according to some embodiments of the present invention.
Figure 33A:
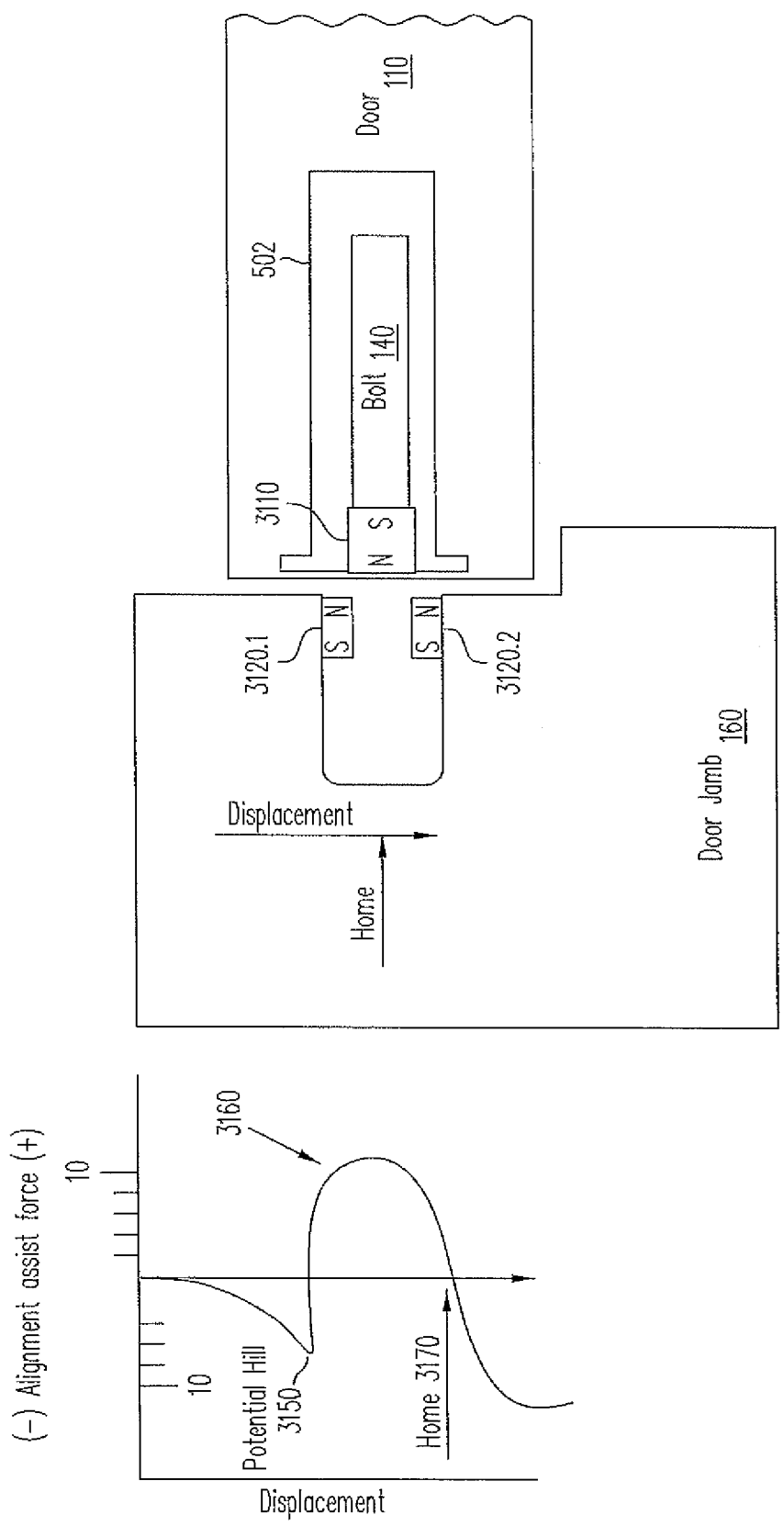
FIG. 33A illustrates a top view and a force/displacement graph of a system for magnetically aligning a bolt with a cavity according to some embodiments of the present invention.

FIGS. 33A (top view) and 33B (side view of door jamb 160) show a similar embodiment but the magnets 3110 and 3120 are arranged to repel each other in the aligned state. Each of magnets 3110, 3120 extends perpendicularly to the door/cavity boundary as in FIG. 31. The same polarity poles (north polarity in FIG. 33) face the interface between the door and the strike plate (the door jamb) in the aligned state. In this state, the north pole of magnet 3110 is between the north poles of magnets 3120.1, 3120.2, so the magnets 3120.1, 3120.2 simultaneously repel the magnet 3110 to simultaneously force the door clockwise and counterclockwise. This is a stable equilibrium as the resultant magnetic force pushes the door into the aligned state if the door moves out of the aligned state either clockwise or counterclockwise. See the force/displacement diagram on the left of FIG. 33A. When the door is being closed, the magnets at first resist the door closing due to the repelling force between the magnets 3110 and 3120, but then (past point 3150) urge the door into the aligned state.

Magnets 3120.1, 3120.2 can be positioned at the opposite sides of the cavity at any height (the height being the vertical dimension in FIG. 33B), and can be wholly or partially inside the cavity or wholly outside of the cavity, perhaps in the strike plate. Magnet 3110 can be positioned in the face plate or some other place. An exemplary north-pole position of magnet 3110 in the aligned state is shown by a dotted line in FIG. 33B. The magnets can be spaced from the bolt and the cavity.

This design provides stiffer centering behavior at home position (i.e. in the aligned state). Like a spring assisted device this design exhibits a potential hill around the point 3150 (whereby one needs to push the door against the potential hill, after which the door will be pulled towards the aligned state by the magnetic forces of magnets 3110, 3120). Some embodiments work well for doors with low to medium friction.

Figure 34:
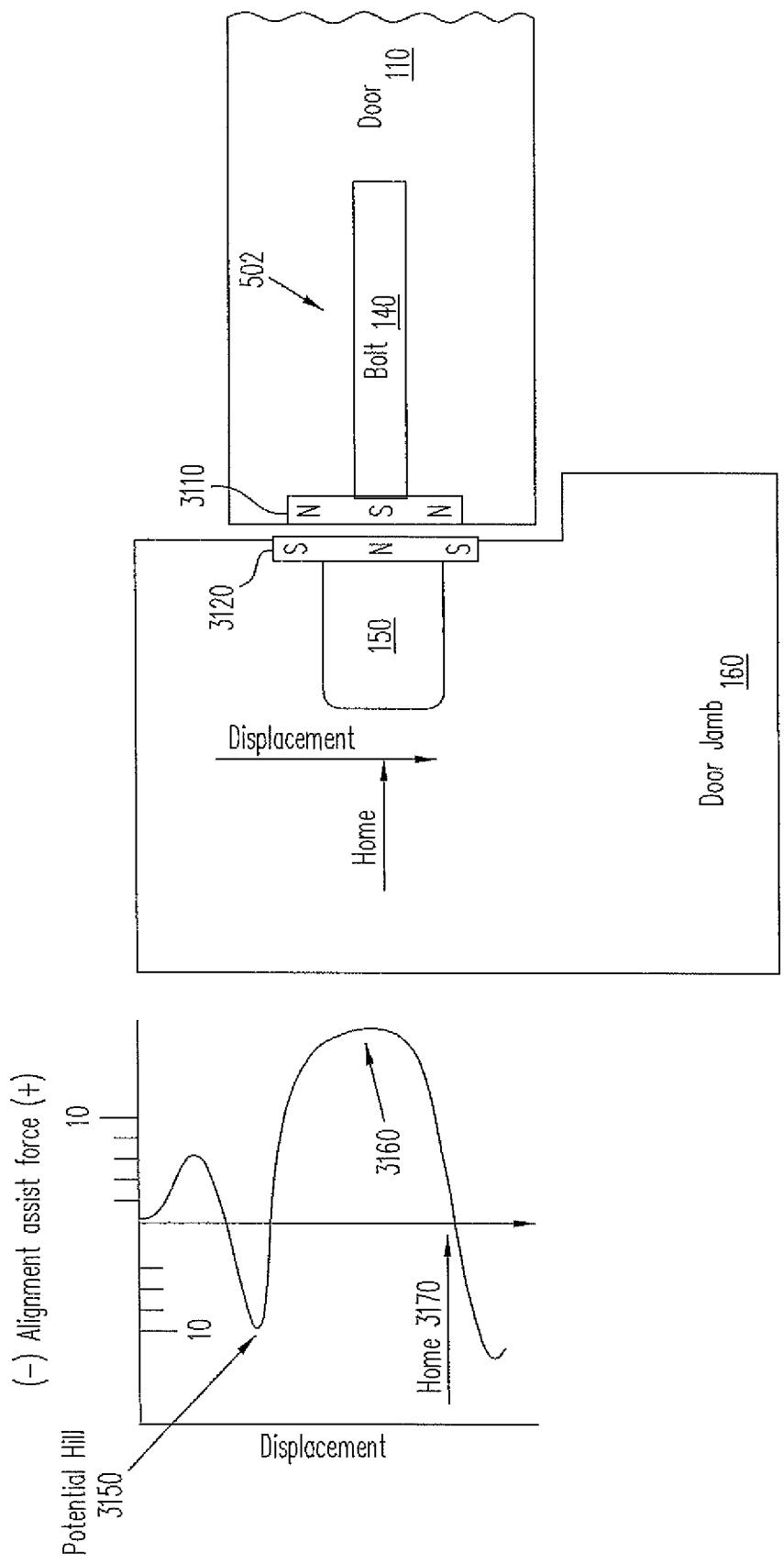
FIGS. 34, 35A each illustrate a top view and a force/displacement graph of a system for magnetically aligning a bolt with a cavity according to some embodiments of the present invention.

FIG. 34 shows a similar embodiment with a multi-polar arrangement that has greater force and displacement compliance. Both magnets 3110, 3120 are bar or strip magnets. Magnet 3110 is an N-S-N magnet, and magnet 3120 is S-N-S magnet. Each magnet's pole is adjacent to the other magnet's pole of the opposite polarity in the aligned state. The magnets can be placed relative to the bolt and cavity in the same positions as described above in connection with FIGS. 32A, 32B. The tactile feedback however may give a false sense of door closure when the door is open and the magnet 3110 first approaches the magnet 3120 in the counterclockwise direction. This arrangement gives modified tactile feedback relative to the scheme in which the door has a spring and roller assisted centering device. Typical force versus displacement behavior of this arrangement is shown in the force/displacement diagram on the left. This arrangement provides stiff centering behavior at home position. Point 3150 in FIG. 34 marks the bottom of the potential hill (whereby one needs to push the door against the potential hill, after which the door will be pulled towards proper alignment due to magnetic force between the magnets on door and strike plate). The arrangement is more resilient to door friction.

Figure 35B:
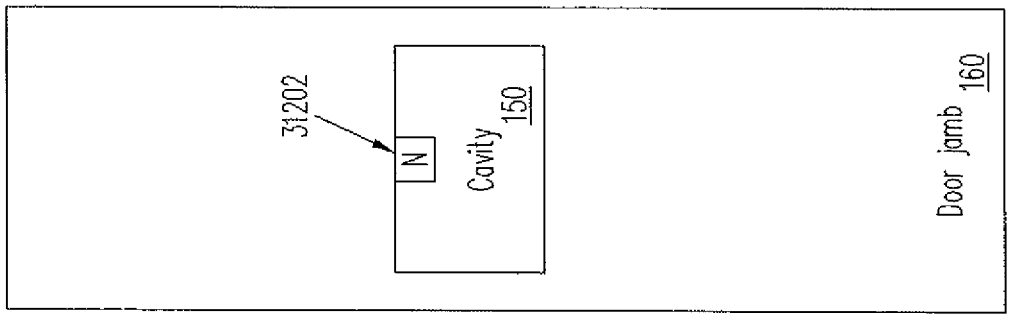
FIG. 35B is a side view of a door jamb of the system of FIG. 35A according to some embodiments of the present invention.
Figure 35A:
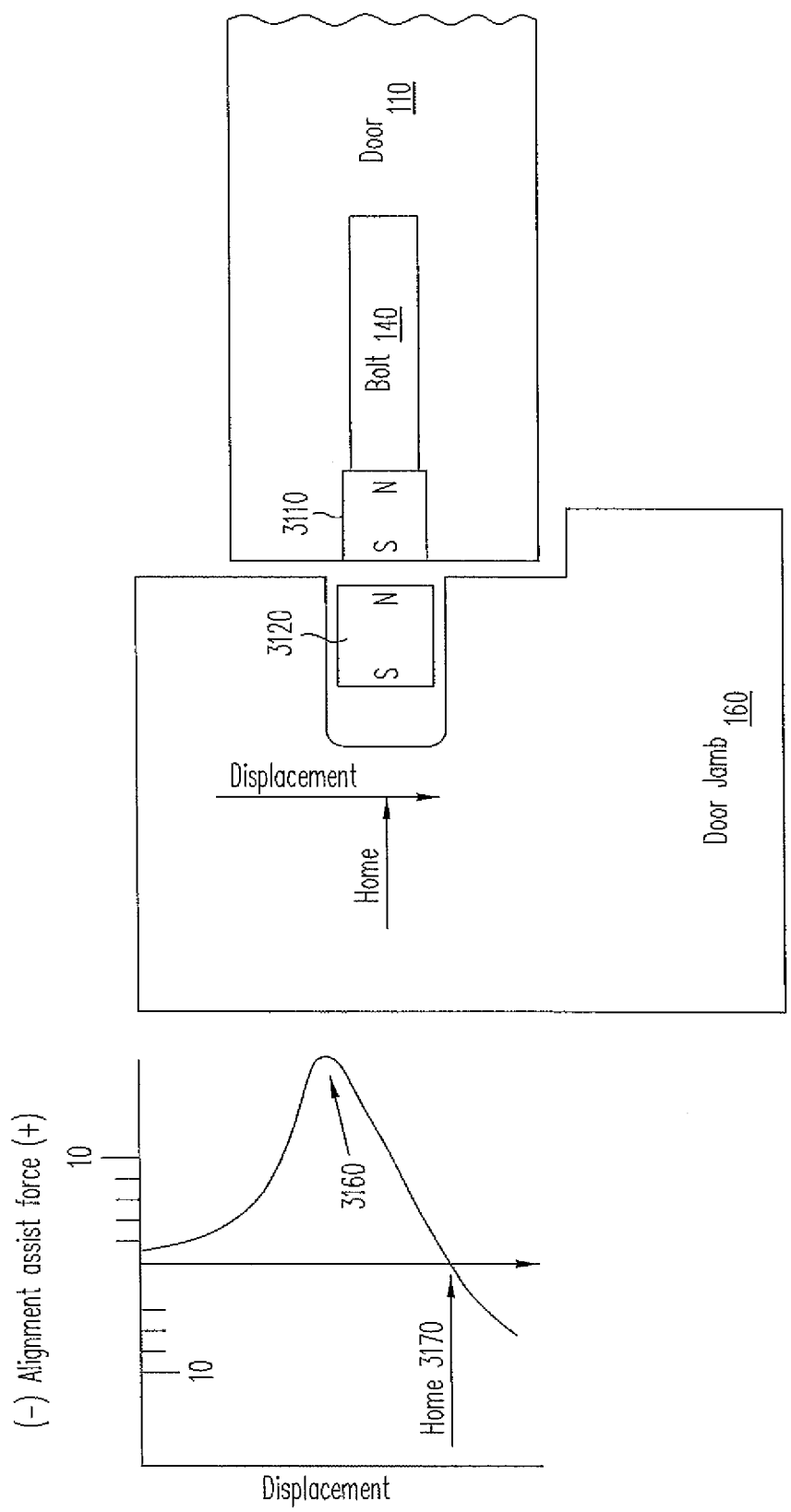

FIGS. 35A (top view) and 35B (side view of door jamb 160) shows a door self-alignment arrangement in which a potential hill is absent so the magnets do not resist the door closing. Typical force versus displacement behavior of this arrangement is shown on the graph on the left of the figure. This arrangement does not give as much alignment stiffness as other schemes, however compared to other topologies discussed, this configuration only has attractive force (to help close the door on the door jamb), and does not increase initial force required to push door in the door jamb. This helps meet regulatory requirements specifying the maximum push force sufficient for door closure. In some embodiments, the arrangement works well for doors with low to medium friction, but high friction embodiments are also possible. One can modify this scheme by employing soft iron instead of magnets on either one side (i.e. door or strike plate).

The magnets can be at the top or bottom of the bolt and cavity (FIG. 35B) or in any other position which does not interfere with the bolt motion. The magnets do not have to be precisely aligned to face each other in the aligned state. The same is true for all of the arrangements described above in connection with FIGS. 31-35.

The alignment assist techniques described above can be used without a lock, if for example a door does not need to be locked but has to stay closed, especially (but not necessarily) if the closed position must be a precise position for any reason.

To reiterate, the invention is not limited to the embodiments described above. The invention includes various embodiments for locking a first object to a second object. In some embodiments, the first and second objects move relative to each other. For example, the first object may be stationary (like a door frame) while the second object may be movable (like a door), or both may be movable, or both objects may be movable (like in a double door). While the invention has been illustrated on the example of the door/lock arrangement of FIG. 1, other lock arrangements and non-door locks can be used as described above. Other embodiments and variations are within the scope of the invention, as defined by the appended claims.

The invention claimed is:

1. An apparatus for providing access, the apparatus comprising an alignment assistance system for a lock assembly which is for locking a first object to a second object, the first and second objects being movable relative to each other, the lock assembly comprising a fastener which is for being installed on the first object and for being operable to engage the second object in an aligned state in which the fastener is aligned with the second object, to lock the first and second objects together in the aligned state;

wherein access is not provided in the aligned state;
wherein access is operable to be provided in at least a first state of the first and second objects, the first state being a non-aligned state;
wherein the first and second objects are for being positioned so that in the aligned state, the first object is movable relative to the second object in at least a first direction and a second direction opposite from the first direction;
wherein movement from the aligned state in the first direction leads to the first state, and wherein movement from the first state back in the second direction causes a return to the aligned state;
wherein the alignment assistance system comprises magnetic material in the first and second objects, the magnetic material being arranged so that at least when the first and second objects are in a vicinity of the aligned state, the magnetic material urges the first and second objects into the aligned state, and when the first and second objects are in the aligned state, then magnetic forces induced by the magnetic material resist the first and second objects moving out of the aligned state in any one of the first and second directions.

2. The apparatus of claim 1 further comprising an alignment sensor system which comprises a sensor for sensing an aligned state at least when the fastener does not engage the second object, the aligned state being a state in which the fastener is aligned with the second object;

the apparatus comprising the lock assembly, wherein the fastener is a bolt, the second object comprises a hole into which the bolt is to extend to engage the second object but from which the bolt retracts to unlock the first object from the second object, wherein the bolt is aligned with the hole in the aligned state, wherein the alignment sensor system comprises:

a light source having an output port; and a reflector to reflect light from the output port at least in the aligned state and to provide reflected light, the reflector being for reflecting more light from the output port in the aligned state than not in the aligned state, the sensor receiving more of the reflected light from the output port in the aligned state than not in the aligned state;

wherein one of the light source and the reflector is for being located in the lock assembly on the first object in, or on, or adjacent to the fastener, and the other one of the light source and the reflector is for being located on the second object.

3. The apparatus of claim 2 wherein the light source is for being located in the lock assembly on the first object in, or on, or adjacent to the fastener, and the reflector is for being located on the second object.

4. The apparatus of claim 1 further comprising an alignment sensor system which comprises a sensor for sensing an aligned state at least when the fastener does not engage the second object, the aligned state being a state in which the fastener is aligned with the second object;

the apparatus comprising the lock assembly, wherein the fastener is a bolt, the second object comprises a hole into which the bolt is to extend to engage the second object but from which the bolt retracts to unlock the first object from the second object, wherein the bolt is aligned with the hole in the aligned state, wherein the alignment sensor system comprises:

a light source having an output port; and a light-suppression member to suppress redirection of light received from the output port to the sensor in the aligned state, the sensor being for receiving less light emitted from the output port and impinging on the light-suppression member in the aligned state than not in the aligned state;

wherein one of the light source and the light-suppression member is for being located in the lock assembly on the first object in, or on, or adjacent to the fastener, and the other one of the light source and the light-suppression member is for being located on the second object.

5. The apparatus of claim 4 wherein the light source is for being located in the lock assembly on the first object in, or on, or adjacent to the fastener, and the light-suppression member is for being located on the second object.

6. The apparatus of claim 1 further comprising an alignment sensor system which comprises a sensor for sensing an aligned state at least when the fastener does not engage the second object, the aligned state being a state in which the fastener is aligned with the second object;

wherein the alignment sensor system comprises a spectral apparatus comprising a light source, the spectral apparatus being for generating at least two alternative spectral properties;

wherein each of the alternative spectral properties is recognizable by the alignment sensor system using the sensor as different from each other one of the alternative spectral properties, and wherein for a plurality of sets of the alternative spectral properties, each set being a set of one of more of the alternative spectral properties, for any set in the plurality, the alignment sensor system is operable to be calibrated to recognize the aligned state upon recognizing any alternative spectral property in the set but not upon recognizing any one of the alternative spectral properties outside of the set.

7. The apparatus of claim 6 further comprising the lock assembly.

8. The apparatus of claim 1 further comprising an alignment sensor system which comprises a sensor for sensing an aligned state at least when the fastener does not engage the second object, the aligned state being a state in which the fastener is aligned with the second object;

wherein the alignment sensor system comprises a beam generation apparatus for generating a plurality of beams, and the sensor comprises a plurality of first sensors each of which is operable to generate an indication of sensing or not sensing at least one of the beams;

wherein the alignment sensor system is operable to recognize, from said indications, which of the first sensors is sensing at least one of said beams and which of the first sensors is not sensing any one of the beams, the alignment sensor system being thus operable to recognize any set of one or more of the first sensors such that each first sensor in the set senses at least one of the beams and each first sensor outside of the set does not sense any one of the beams;

wherein for a plurality of said sets, for each set in the plurality of sets, the alignment sensor system is operable to be calibrated to recognize the aligned state upon recognizing said set but not upon recognizing at least one other set in the plurality of sets.

9. The apparatus of claim 8 further comprising the lock assembly.

10. The apparatus of claim 1 further comprising an alignment sensor system which comprises a sensor for sensing an aligned state at least when the fastener does not engage the second object, the aligned state being a state in which the fastener is aligned with the second object;

the apparatus comprising the lock assembly, wherein the fastener is a bolt, the second object comprises a hole into which the bolt is to extend to engage the second object but from which the bolt retracts to unlock the first object from the second object, wherein the bolt is aligned with the hole in the aligned state;

wherein the bolt has a first end ("engaging end") which is to engage the second object to lock the first object to the second object, and the bolt has a second end opposite from the first end;

wherein the apparatus further comprises a bolt-position sensor system for sensing whether or not the bolt is extended, the bolt-position sensor system comprising a sensor located closer to the second end than to the engaging end to sense whether or not the bolt is extended;

the apparatus further comprising circuitry for generating a lock-indication signal indicative of a locked state in which the lock locks the first object to the second object, the lock-indication signal being generated in response to the alignment sensor system sensing the aligned state and the bolt-position sensor system sensing that the bolt is extended.

11. The apparatus of claim 1 further comprising an alignment sensor system which comprises a sensor for sensing an aligned state at least when the fastener does not engage the second object, the aligned state being a state in which the fastener is aligned with the second object;
the apparatus comprising the lock assembly, wherein the fastener is a bolt, the second object comprises a hole into which the bolt is to extend to engage the second object but from which the bolt retracts to unlock the first object from the second object, wherein the bolt is aligned with the hole in the aligned state;
wherein the bolt has a first end ("engaging end") which is to engage the second object to lock the first object to the second object, and the bolt has a second end opposite from the first end;
wherein the lock assembly comprises a dead-latch bar coordinated with the bolt such that when the bolt is extended and the dead-latch bar is retracted, the lock assembly provides increased resistance to retracting the bolt by pressing on the engaging end;
wherein the apparatus further comprises a position sensor system for sensing the position of at least one of the bolt and dead-latch bar, the position sensor system comprising a sensor located closer to the second end than to the engaging end to sense the position of at least one of the bolt and dead-latch bar.

12. The apparatus of claim 11 further comprising circuitry for generating a lock-indication signal indicative of a locked state in which the lock locks the first object to the second object, the lock-indication signal being generated if the alignment sensor system sensing the aligned state and the position sensor system sensing that the bolt is extended and/or the dead-latch bar is retracted.

13. The apparatus of claim 1 further comprising a position sensor system for the lock assembly, wherein the fastener is a bolt;
wherein the second object comprises a hole into which the bolt is to extend to engage the second object but from which the bolt retracts to unlock the first object from the second object;
wherein the bolt has a first end ("engaging end") which is to engage the second object to lock the first object to the second object, and the bolt has a second end opposite from the first end;
wherein the lock assembly comprises a dead-latch bar coordinated with the bolt such that when the bolt is extended and the dead-latch bar is retracted, the lock assembly provides increased resistance to retracting the bolt by pressing on the engaging end;
wherein the position sensor system is for sensing the position of the dead-latch bar;
wherein the position sensor system comprises a sensor located closer to the second end than to the engaging end for sensing the position of the dead-latch bar.

14. The apparatus of claim 1 wherein the magnetic material comprises:
a first magnet in the first object; and
a second magnet in the second object;
wherein in the aligned state the first and second magnets attract each other.

15. The apparatus of claim 1 further comprising an apparatus for generating a signal signaling the presence of the aligned state, and for driving the fastener to engage the second object in response to the signal, and for not driving the fastener to engage the second object in the absence of the signal.

16. The apparatus of claim 1 wherein the magnetic material in the first object is positioned immediately adjacent to the fastener.

17. The apparatus of claim 1 wherein the second object comprises a cavity for engaging the fastener to lock the first and second objects in the aligned state, wherein the magnetic material in the second object is positioned in the cavity and/or immediately adjacent to the cavity.

18. The apparatus of claim 1 wherein the aligned state does not allow the first and second objects to physically contact each other.

19. The apparatus of claim 1 wherein in the aligned state, the magnetic material in the first object is spaced from the magnetic material in the second object.

20. An apparatus comprising an alignment assistance system for a lock assembly which is for locking a first object to a second object, the first and second objects being movable relative to each other, the lock assembly comprising a fastener which is for being installed on the first object and for being operable to engage the second object in an aligned state in which the fastener is aligned with the second object, to lock the first and second objects together in the aligned state;
wherein the first and second objects are for being positioned so that in the aligned state, the first object is movable relative to the second object in at least two opposite directions;
wherein the alignment assistance system comprises magnetic material in the first and second objects, the magnetic material being arranged so that at least when the first and second objects are in a vicinity of the aligned state, the magnetic material urges the first and second objects into the aligned state, and when the first and second objects are in the aligned state, then the magnetic material resists the first and second objects moving out of the aligned state in any one of the two opposite directions;
wherein the magnetic material comprises at least three magnets each of which is located in one of the first and second objects, each of the first and second objects comprising at least one of the magnets;
wherein the magnets are arranged so that in the aligned state, at least two of the magnets in one of the first and second objects repel at least one of the magnets on the other one of the first and second objects to simultaneously force the first object into both of the two opposite directions relative to the second object.

21. A method comprising operating a lock assembly for providing access, wherein the lock assembly is for locking a first object to a second object, the first and second objects being movable relative to each other, the lock assembly comprising a fastener installed on the first object and operable to engage the second object in an aligned state in which the fastener is aligned with the second object, to lock the first and second objects together in the aligned state;
wherein access is not provided in the aligned state;
wherein access is operable to be provided in at least a first state of the first and second objects, the first state being a non-aligned state;
wherein in the aligned state, the first object is movable relative to the second object in at least a first direction and a second direction opposite from the first direction;

wherein movement from the aligned state in the first direction leads to the first state, wherein movement from the first state back in the second direction causes a return to the aligned state;

wherein the alignment assistance system comprises magnetic material in the first and second objects, the magnetic material being arranged so that at least when the first and second objects are in a vicinity of the aligned state, the magnetic material urges the first and second objects into the aligned state, and when the first and second objects are in the aligned state, then magnetic forces induced by the magnetic material resist the first and second objects moving out of the aligned state in any one of the first and second directions;

the method comprising urging at least one of the first and second objects towards the aligned state, the urging being performed by the magnetic material in the first and second objects.

22. The method of claim 21 wherein the magnetic material comprises:
a first magnet in the first object; and
a second magnet in the second object;
wherein in the aligned state the first and second magnets attract each other.

23. The method of claim 21 further comprising generating a signal signaling the presence of the aligned state, and driving the fastener to engage the second object in response to the signal;
wherein the fastener is not driven to engage the second object in the absence of the signal.

24. The method of claim 21 wherein the magnetic material in the first object is positioned immediately adjacent to the fastener.

25. The method of claim 21 wherein the second object comprises a cavity for engaging the fastener to lock the first and second objects in the aligned state, wherein the magnetic material in the second object is positioned in the cavity and/or immediately adjacent to the cavity.

26. The method of claim 21 wherein the aligned state does not allow the first and second objects to physically contact each other.

27. The method of claim 21 wherein in the aligned state, the magnetic material in the first object is spaced from the magnetic material in the second object.

28. A method comprising operating a lock assembly which is for locking a first object to a second object, the first and second objects being movable relative to each other, the lock assembly comprising a fastener installed on the first object and operable to engage the second object in an aligned state in which the fastener is aligned with the second object, to lock the first and second objects together in the aligned state;

wherein in the aligned state, the first object is movable relative to the second object in at least two opposite directions;

wherein the alignment assistance system comprises magnetic material in the first and second objects, the magnetic material being arranged so that at least when the first and second objects are in a vicinity of the aligned state, the magnetic material urges the first and second objects into the aligned state, and when the first and second objects are in the aligned state, then the magnetic material resists the first and second objects moving out of the aligned state in any one of the two opposite directions;

the method comprising urging at least one of the first and second objects towards the aligned state, the urging being performed by the magnetic material in the first and second objects;

wherein the magnetic material comprises at least three magnets each of which is located in one of the first and second objects, each of the first and second objects comprising at least one of the magnets;

wherein the magnets in the aligned state, at least two of the magnets in one of the first and second objects repel at least one of the magnets on the other one of the first and second objects to simultaneously force the first object into both of the two opposite directions relative to the second object.

* * * * *